United States Patent
Camus et al.

(10) Patent No.: US 7,865,003 B2
(45) Date of Patent: Jan. 4, 2011

(54) IMAGE EVALUATION METHOD FOR TWO-DIMENSIONAL PROJECTION IMAGES AND OBJECTS CORRESPONDING THERETO

(75) Inventors: Estelle Camus, Mountain View, CA (US); Thomas Redel, Poxdorf (DE)

(73) Assignee: Siemens Aktiengesellschaft, Munich (DE)

(*) Notice: Subject to any disclaimer, the term of this patent is extended or adjusted under 35 U.S.C. 154(b) by 887 days.

(21) Appl. No.: 11/809,073

(22) Filed: May 31, 2007

(65) Prior Publication Data

US 2007/0297658 A1    Dec. 27, 2007

(30) Foreign Application Priority Data

May 31, 2006    (DE) .................. 10 2006 025 422

(51) Int. Cl.
G06K 9/00 (2006.01)
A61B 5/02 (2006.01)
(52) U.S. Cl. .................... 382/128; 600/481
(58) Field of Classification Search .......... 382/128, 382/129, 130, 131, 132, 133, 134; 600/324, 600/381, 407, 462, 467, 479, 481, 483, 513; 606/158, 194; 378/4, 8, 901; 128/920, 922

See application file for complete search history.

(56) References Cited

U.S. PATENT DOCUMENTS 6,854,884 B2 *    2/2005    Kerrien et al. .............. 378/207

(Continued)

FOREIGN PATENT DOCUMENTS

DE        100 00 185 A1    7/2001

(Continued)

OTHER PUBLICATIONS

Thomas Wittenberg, Peter Hastreiter, Ulrich Hoppe, Heinz Handels, Alexander Horsch, Hans-Peter Meinzer; "Bildverarbeitung für die Medizin 2003—Algorithmen—Systeme—Anwendungen"; Proceedings des Workshops, Mar. 9-11, 2003; pp. 80-85; Springer; Erlangen, Germany.

(Continued)

Primary Examiner—Abolfazl Tabatabai

(57) ABSTRACT

2-D projection images show the temporal profile of the distribution of a contrast medium in an examination object, which contains a vascular system and its surroundings. Each projection image comprises pixels with pixel values. The pixel values of pixels corresponding to one another in the projection images are defined by at least essentially locationally identical areas of the examination object. A computer assigns a uniform 2-D evaluation core that is uniform for all corresponding pixels at least in a sub-area of pixels corresponding to one another in the projection images that is uniform for the projection images. The computer defines at least one characteristic value for each pixel within each projection image based on the evaluation core assigned to the pixel and assigns it to the relevant pixel. Based on the temporal profile of the characteristic values, the computer defines parameters of at least one function of time, so that any deviation between the function parameterized with the parameters and the temporal profile of the characteristic values is minimized. Based on the parameters the computer defines a type and/or an extent and assigns them to a pixel of a 2-D evaluation image corresponding to the pixels of the projection images. The type indicates whether the respective pixel of the evaluation image corresponds to a vessel of the vascular system, a perfused part or a non-perfused part of the surroundings of a vessel of the vascular system. The extent is characteristic of perfusion. The computer outputs at least the sub-area of the evaluation image to a user via a display device.

25 Claims, 24 Drawing Sheets

U.S. PATENT DOCUMENTS

| | | |
|---|---|---|
| 7,336,760 B2 * | 2/2008 | Virshup et al. .................. 378/7 |
| 2003/0114759 A1 | 6/2003 | Skyba et al. |
| 2007/0041625 A1 | 2/2007 | Camus et al. |

FOREIGN PATENT DOCUMENTS

| | | |
|---|---|---|
| DE | 101 00 572 A1 | 7/2002 |
| DE | 101 07 765 A1 | 8/2002 |
| DE | 10 2005 036 875 A1 | 5/2006 |
| DE | 10 2005 039 189 A1 | 2/2007 |
| EP | 1 302 163 A2 | 4/2003 |
| EP | 1 585 058 A2 | 10/2005 |
| WO | WO 97/17673 A1 | 5/1997 |

OTHER PUBLICATIONS

Malsch et al., Quantitative Analyse von koronarangiographischen Bildfolgen zur Bestimmung der Myokardperfusion in Bildverarbeitung für die Medizin 2003-Algorithmen—Systeme—Anwendungen, Springer-Verlag, ISBN 3-540-00619, pp. 81-85.

* cited by examiner

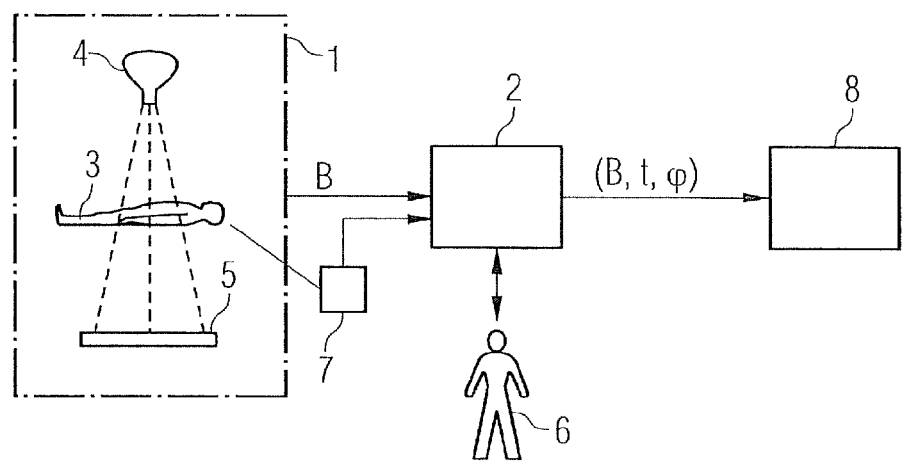
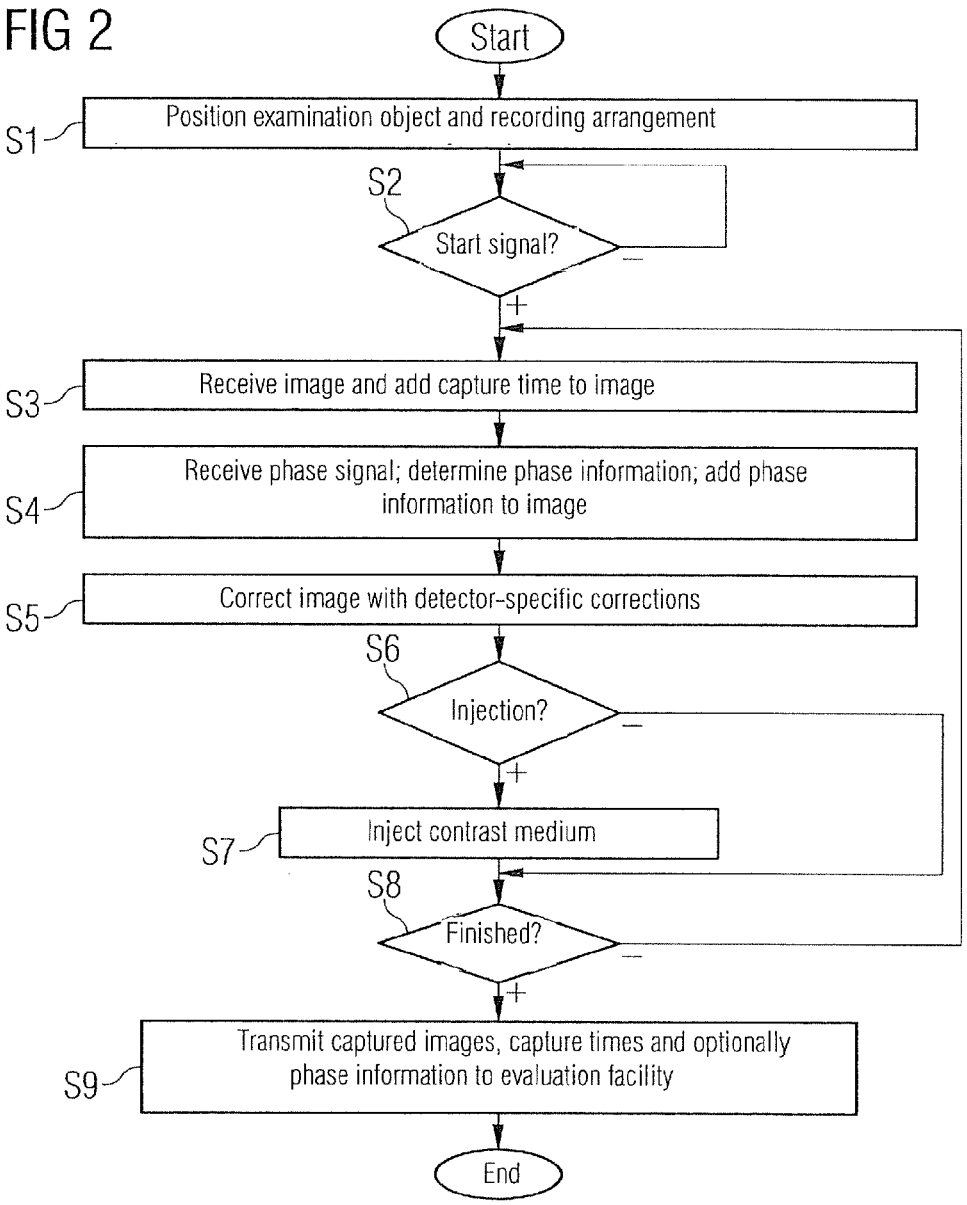

- Object vessel
- Object background
- Perfusion low
- Perfusion moderate
- Perfusion high

SW1=....
GZP=.....
F=........

FIG 8
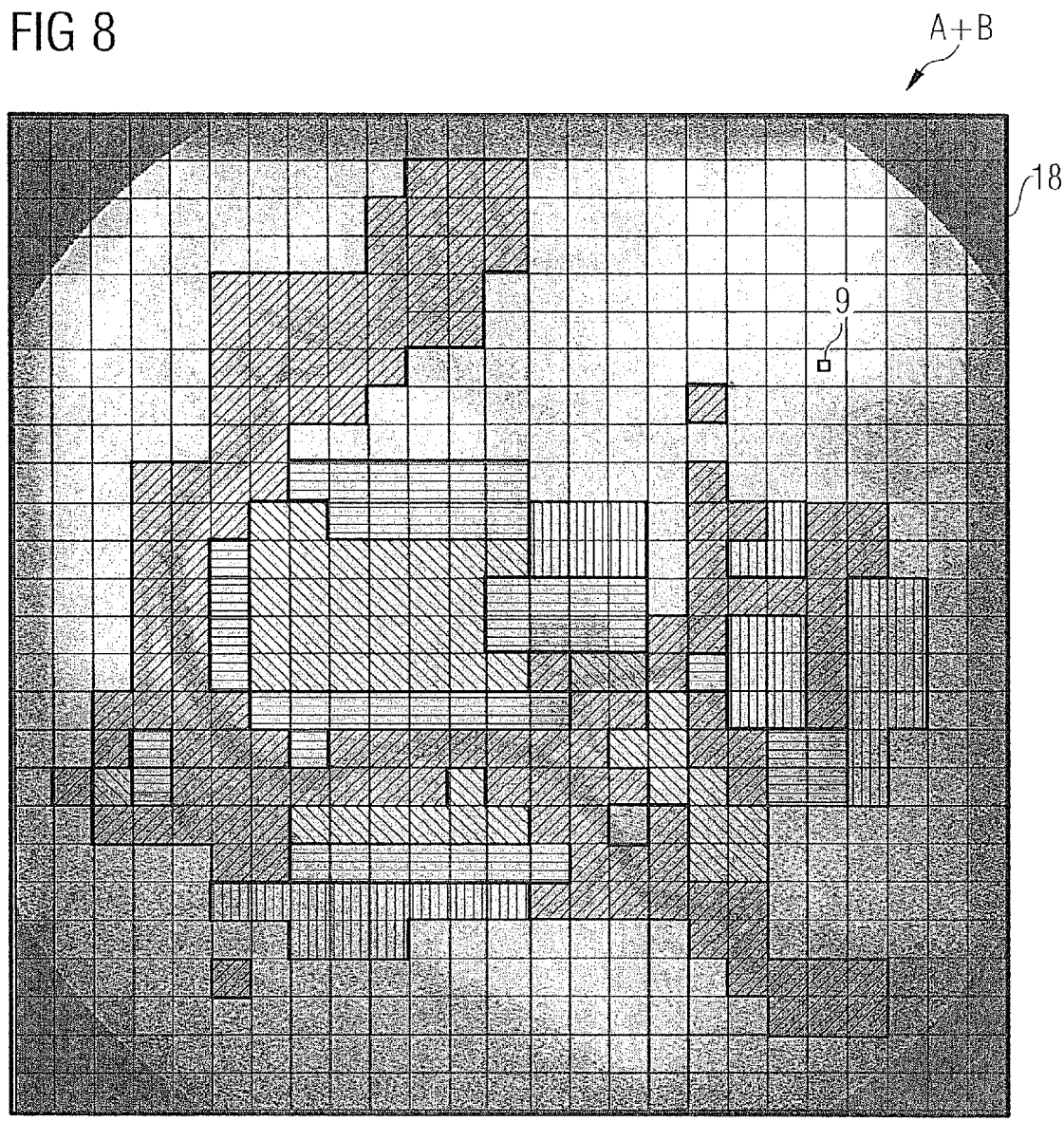
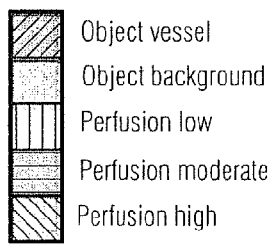
Object vessel
Object background
Perfusion low
Perfusion moderate
Perfusion high

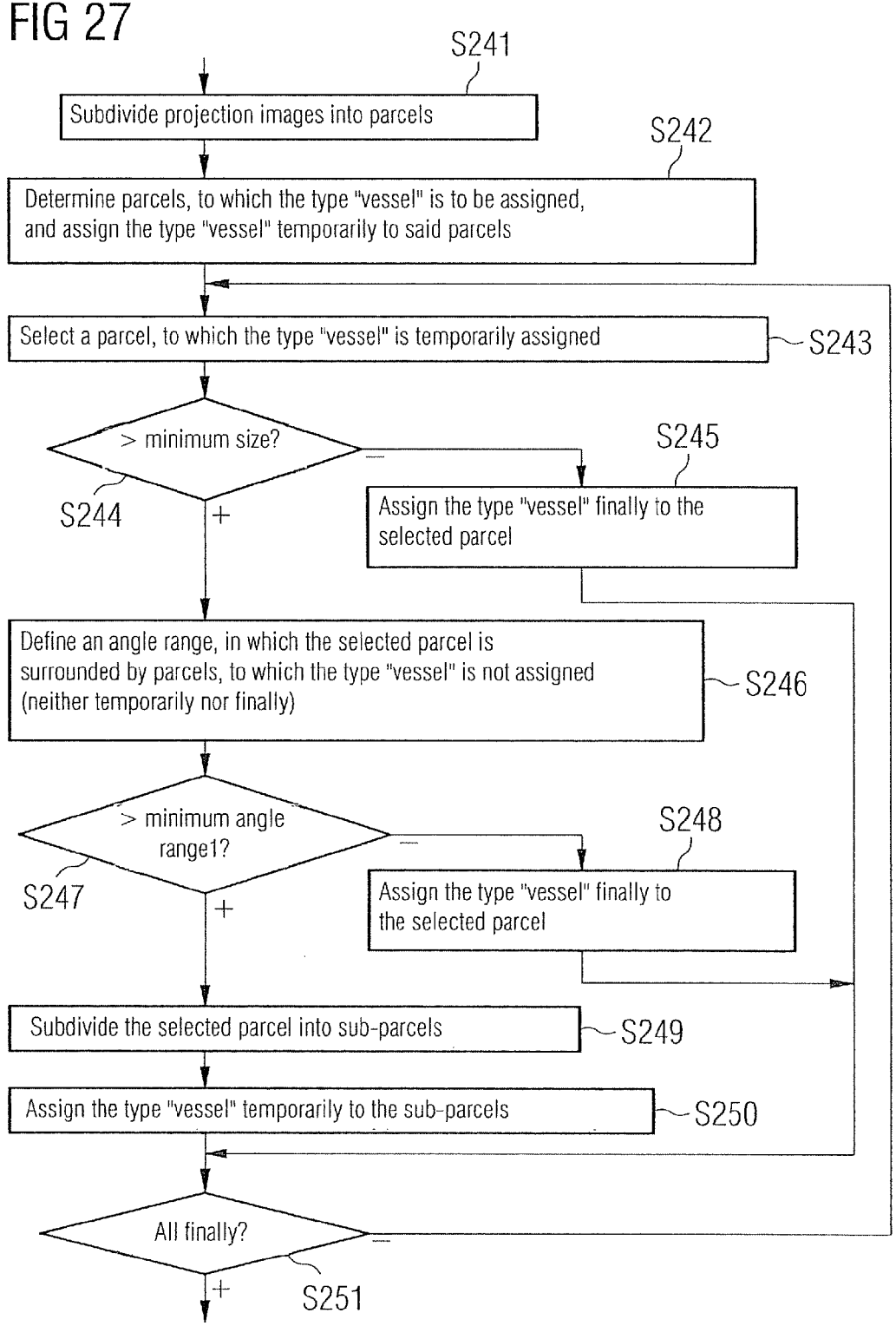

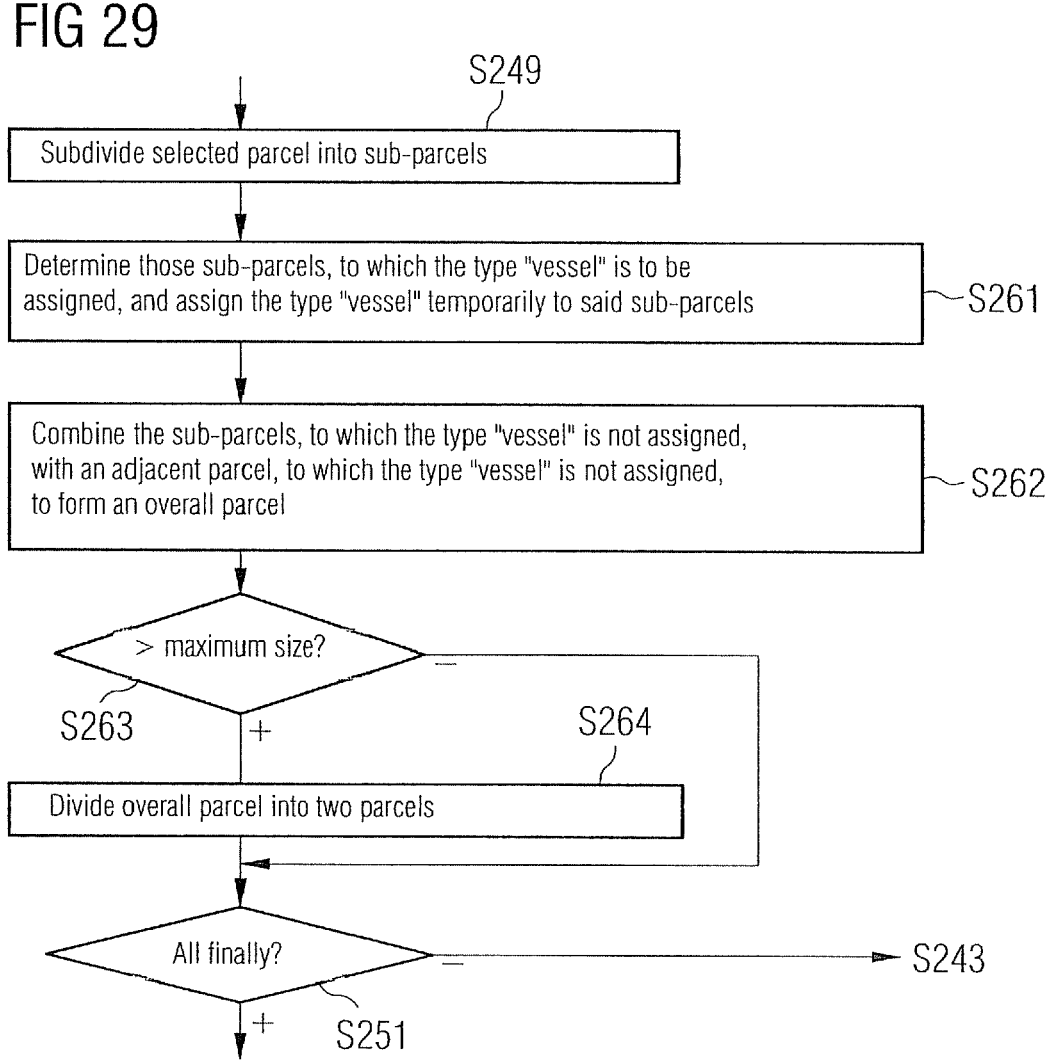

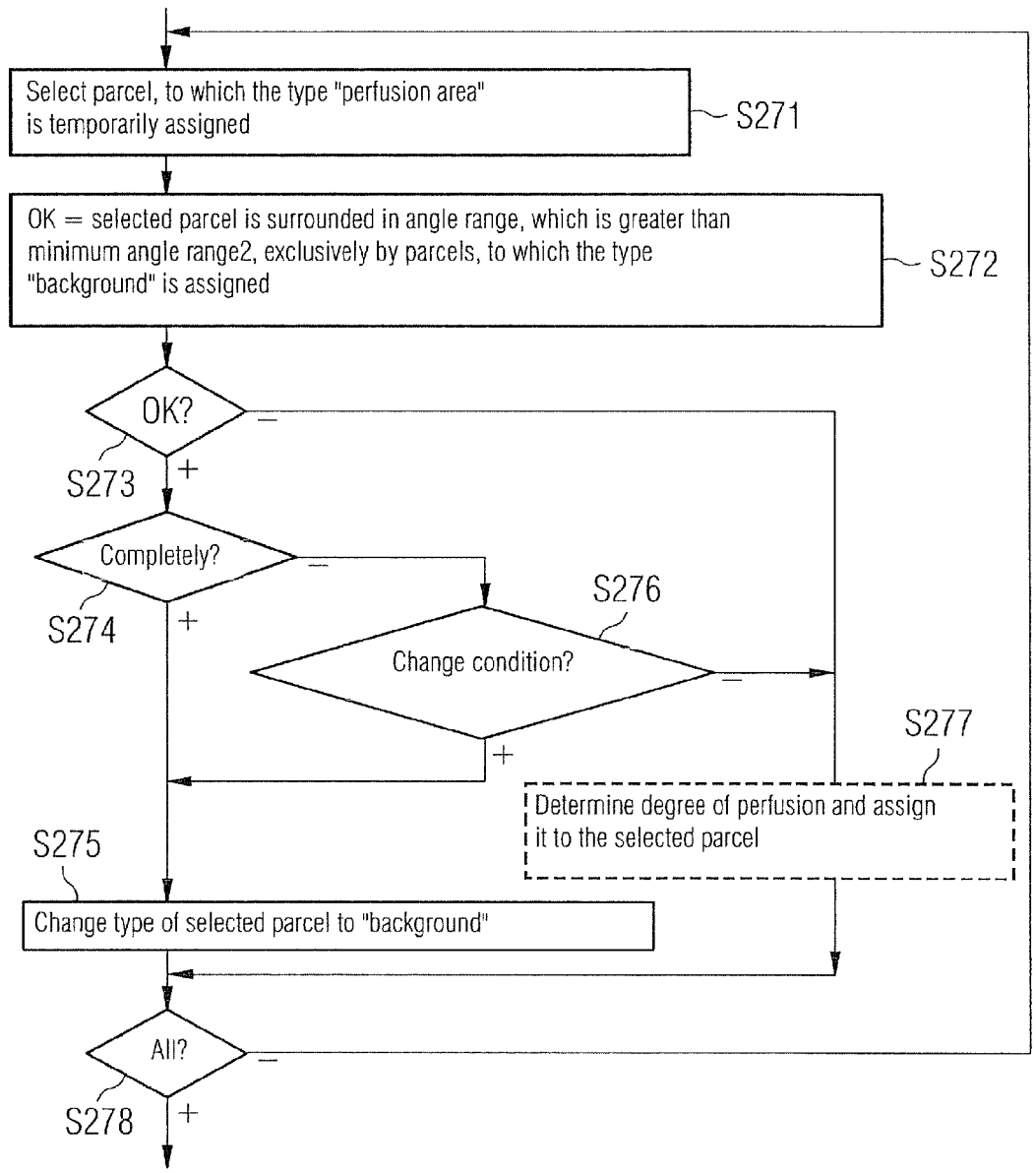

IMAGE EVALUATION METHOD FOR TWO-DIMENSIONAL PROJECTION IMAGES AND OBJECTS CORRESPONDING THERETO

CROSS REFERENCE TO RELATED APPLICATIONS

This application claims priority of German application No. 10 2006 025 422.8 DE filed May 31, 2006, which is incorporated by reference herein in its entirety.

FIELD OF INVENTION

The present invention relates to an image evaluation method for two-dimensional projection images, which show the temporal profile of the distribution of a contrast medium in an examination object, the examination object containing a vascular system and its surroundings, each projection image comprising a plurality of pixels having pixel values, the pixel values of pixels corresponding to one another in the projection images being defined by at least essentially locationally identical areas of the examination object.

The present invention relates furthermore to a data medium with a computer program stored on the data medium for implementing an image evaluation method of this type and to a computer with a mass memory in which a computer program is filed, such that the computer executes an image evaluation method of this type after the computer program has been called.

BACKGROUND OF INVENTION

Image evaluation methods of this type and the corresponding objects (data medium with computer program, programmed computer) are known.

Thus, for example, an image evaluation method of this type is known from the technical article "Quantitative Analyse von koronarangiographic Bildfolgen zur Bestimmung der Myokardperfusion" [Quantitative analysis of coronary angiographic image sequences for determining myocardial perfusion] by Urban Malsch et al., which appeared in "Bildverarbeitung fur die Medizin 2003—Algorithmen—Systeme—Anwendungen" [Image processing for medicine 2003—algorithms—systems—applications], Springer Verlag, pages 81 to 85. With this image evaluation method, a computer uses the projection images to determine a two-dimensional evaluation image, which comprises a plurality of pixels, and outputs the evaluation image to a user via a display device. The pixels of the evaluation image correspond to those of the projection images. The computer uses the temporal profile of the pixel values of the projection images to assign a pixel value to the pixels of the evaluation image, the pixel value being characteristic of the time of maximum contrast change.

The doctrine of the above-mentioned technical article is described in the context of angiographic examinations of the coronary arteries of the human heart. This type of examination is one of the most important diagnostic tools in cardiology today. Additional information such as the determination of flow velocity or myocardial perfusion is further information which can in principle be obtained by means of angiography. The essential diagnostic evidence here is the perfusion of the cardiac muscle.

Today, a number of other non-invasive methods of examination such as PET, SPECT, MR or contrast-medium-aided ultrasound have also become established. These methods of examination offer the facility for quantifying, in addition to other parameters, the perfusion status of the myocardium. These methods are generally applied in stable angina pectoris cases or in order to assess the risk after a myocardial infarction.

For an assessment of the therapeutic outcome of an intervention, it would therefore be advantageous to be able to monitor the improvement in perfusion and/or the occurrence of microembolization and microinfarctions during the actual intervention. It would consequently be advantageous if quantification of perfusion were added to the other diagnostic parameters in the catheter laboratory, as this would make it possible to obtain all relevant information in one examination and thus to achieve an improvement in the monitoring of treatment.

Quantification of the supply of blood to the myocardium by means of angiographic methods is however problematic, since the angiographically observable cardiac vessels have a diameter of just under a millimeter or more. These observable vessels terminate in millions of tiny capillary vessels, which have diameters of only a few micrometers. The flow dynamics and distribution in the capillary vessels are ultimately determined by the blood supply to the cardiac muscle. Drawing conclusions from the macroscopic supply of blood as to the dynamics of the supply of blood in the capillary vessels is, strictly speaking, inadmissible, even though it is often done.

In order to capture the supply of blood to the myocardium, various methods are known, in particular contrast echocardiography, magnetic resonance tomographic diagnostics and SPECT.

In order to make the blood flow dynamics in large vessels and in the capillary vessels measurable and thereby comparable, various gradation systems are known which divide up the continuum of conditions into discrete classes. Some of these classifications describe the macroscopic circulation of blood, others the circulation of blood in the capillaries. The most commonly used classifications were drawn up by the scientific organization "Thrombolysis in Myocardial Infarction" (TIMI). These classifications are deemed to be the standard. In multi-center studies in which reproducible and comparable results are of particular importance, the TIMI classifications are frequently used. The classifications are complex and can be applied only in a time-consuming manner. They are therefore not generally used in routine clinical work.

By far the most frequently used method in the prior art is the visual assessment of "myocardial blush" on a screen. This procedure is often used for multi-center studies. A prerequisite for this procedure is that the angiographic recording is long enough, in order to be able to see the input and washout of the contrast medium. The visual assessment requires a lot of experience and is in practice carried out only by TIMI-blush experts, as they are known.

Various procedures are also known, in which an attempt is made to carry out this subjective and personal visual assessment with the aid of computers. An example is to be found in the above-mentioned technical article by Urban Malsch et al.

The procedure in the above-mentioned technical article represents a good initial approach but still displays shortcomings. For example it is particularly necessary to identify the vessels of the vascular system in the projection images in order to mask out these vessels when evaluating the "myocardial blush". It is also necessary in the case of the procedure in the technical article to work with DSA images. This gives rise to a significant risk of artifacts, to avoid which computation-intensive methods are in turn required in order to compensate for motion.

Image evaluation methods for two-dimensional projection images are also described in the German patent application DE 10 2005 039 189.3. At the date of filing of the present invention said patent application is not yet available to the public and therefore does not represent a general prior art. Said patent application is only to be taken into account in the context of the examination as to novelty in the German procedure for granting patents.

SUMMARY OF INVENTION

The present invention is based on the doctrine of DE 10 2005 039 189.3. The doctrine of DE 10 2005 039 189.3 is described in detail below in conjunction with FIGS. 1 to 18.

In accordance with FIG. 1, a recording arrangement 1 is controlled by a control facility 2. The recording arrangement 1 is used to capture images B of an examination object 3. In the present case, in which the examination object 3 is a person, images B of the heart or of the brain of the person 3 are captured for example.

In order to capture the images B, the recording arrangement 1 has a radiation source 4, here for example an X-ray source 4, and a corresponding detector 5.

In order to capture the images B, the examination object 3 and the recording arrangement 1 are firstly positioned in a step S1, as shown in FIG. 2. Positioning can depend in particular on which region (heart, brain, etc.) of the examination object 3 is to be captured and which part of the region is specifically relevant, for example which coronary artery (RCA, LAD, LCX) is to be observed. Step SI can alternatively be carried out purely manually by a user 6, fully automatically by the control facility 2 or by the user 6 assisted by the control facility 2. The performance of step SI may be associated with a recording of control images.

The control facility 2 then waits in a step S2 for a start signal from the user 6. After the start signal has been received, the detector 5 captures an image B of the examination object 3 and feeds it to the control facility 2. The control facility 2 receives the image B in a step S3 and adds to the image B a corresponding capture time t. If the examination object 3 or the relevant part of the examination object 3 should move iteratively, in a step S4 the control facility 2 also receives a phase signal of the examination object 3 from a corresponding capture facility 7.

Also as part of step S4, the control facility 2 determines corresponding phase information $\phi$ and adds the phase information $\phi$ to the captured image B. For example, the control facility 2 can, as part of step S4, receive an ECG signal and derive the phase information $\phi$ therefrom. Also the control facility 2 can optionally control the recording arrangement 1 based on the phase signal supplied, such that the capturing of the images B takes place only at one or more predefined phase positions of the examination object 3, for example only 0.3 and 0.6 seconds after the R-wave of the ECG signal.

As a rule, the examination object 3 is not influenced externally in its iterative motion. If for example the heart of the person 3 is beating very irregularly, an external stimulation of the heart can take place with a cardiac pacemaker, in order to force a regular heartbeat.

In a step S5, the control facility 2 corrects the captured image B. The control facility 2 preferably corrects the captured image B exclusively with detector-specific corrections but does not carry out any more far-reaching image processing. For example it does not apply any noise-reduction methods.

In a step S6, a check is carried out to establish whether an injection of a contrast medium is to be made. If this check is answered in the affirmative, the contrast medium is injected into the examination object 3 in a step S7. Steps S6 and S7 can—like step S1—be carried out by the user 6 themselves, be performed fully automatically by the control facility 2 or be carried out by the user 6 but aided by the control facility 2.

In a step S8, the control facility 2 checks whether the capturing of the images B is to be terminated. If this is not the case, the control facility 2 goes back to step S3. Otherwise in a step S9 it transmits the captured images B, preferably corrected with detector-specific corrections, their capture times t and optionally also their phase information $\phi$ to an evaluation facility 8. As an alternative to the transmission of the images B, the capture times t and the phase information (p, as part of the subordinate step S9, the transmission could of course also be carried out image by image, i.e. between steps S5 and S6.

The method outlined above was sketched out roughly in DE 10 2005 039 189.3, as it is of only secondary importance within the scope of the invention there. Thus for example the—manual, fully automatic or computer-aided—adjustment of the recording parameters of the recording arrangement 1 (operating voltage of the radiation source 4, image rate, image pre-processing, positioning, etc.) was taken as self-evident. Any necessary calibration of the recording arrangement I was also not examined in more detail. It also goes without saying that the capturing of the images B has to be carried out over a sufficiently long period, namely starting before injection of the contrast medium and ending after washout of the contrast medium.

FIG. 3 shows one of the captured images B by way of example. It can immediately be seen from FIG. 3 that the image B is two-dimensional and contains a plurality of pixels 9. The resolution of the image B is even so high that the individual pixels 9 are no longer identifiable in the image B shown. One of the pixels 9 is marked with the reference symbol 9 purely by way of example. Each pixel 9 has a pixel value which lies for example between 0 and 255 ($=2^8-1$).

It can also be seen from FIG. 3 that the examination object 3 contains a vascular system and its surroundings. Due to the fact that in their entirety the images B form a time sequence, the images B consequently show the temporal profile of the distribution of the contrast medium in the examination object 3.

If the examination object 3 was motionless during the capturing of the images B (for example because images B of the brain of the person 3 were recorded) or if, due to corresponding triggering of the recording (for example always 0.6 seconds after the R-wave of the ECG), the images B constantly show the examination object 3 in the same phase position, image capturing as such already guarantees that the pixel values of pixels 9 corresponding to one another in the images B are defined by at least essentially locationally identical areas of the examination object 3. In this case, all the captured images B can be defined as projection images B within the meaning of the comments that follow. Otherwise an appropriate selection must be made. This is explained in detail below in conjunction with FIGS. 4 and 5.

In accordance with FIG. 4, the evaluation facility 8—which can in principle be identical to the control facility 2—comprises inter alia a computation unit 10 and a mass memory 11. A computer program 12 is filed in the mass memory 11. When the computer program 12 is called, the evaluation facility 8 executes an image evaluation method which is described in detail below. The evaluation facility 8 constitutes a computer within the meaning of the invention there. It should also be mentioned that the computer program 12 must of course previously have been routed to the evaluation facility 8. Routing can for example be carried out by means of a suitable data medium 13, on which the computer program 12 is stored. The data medium 13 is introduced into a suitable interface 14 of the evaluation facility 8, so that the computer program 12 stored on the data medium 13 can be read out and filed in the mass memory 11 of the evaluation facility 8.

In accordance with FIG. 5, the images B are fed to the evaluation facility 8 in a step S11 via a corresponding interface 15. The same applies to the corresponding capture times t and the assigned phase information $\phi$.

In order to select the projection images B from the captured series of images B, the corresponding selection criteria $\phi^*$, $\delta\phi$, namely a reference phase position $\phi^*$ and a phase boundary $\delta\phi$, must also be known to the evaluation facility 8. It is possible here for the reference phase $\phi^*$ and the phase boundary $\delta\phi$ to be stored within the evaluation facility 8. In accordance with FIG. 5, the reference phase $\phi^*$ and the phase boundary $\delta\phi$ are preferably predefined for the evaluation facility 8 in a step S12 by the user 6 via an appropriate input device 17. For example it is possible for the user 6, by means of appropriate inputs, to scroll through the captured sequence of images B and to select one of the images B. The phase information $\phi$ of the image B selected in this way defines the reference phase $\phi^*$ and the distance to the immediately succeeding and immediately preceding image B defines the phase boundary $\delta\phi$. It is equally possible for the user 6 to predefine the corresponding values $\phi^*$, $\delta\phi$ explicitly by means of numerical values. Finally it is possible for the ECG signal to be output to the user 6 via a display device 16 and for the user 6 to place corresponding markers in the ECG signal. In all cases, the user 6 can predefine the values $\phi^*$ and $\delta\phi$ alternatively as absolute time values or as relative phase values.

In steps S13 to S17, the actual selection of the projection images B from the entire series of images B takes place. To this end in step S13 an index i is set to the value one. The evaluation facility 8 then selects the images B of the iteration i of the examination object 3 in step S14. Within the images B now selected, the evaluation facility 8 generally defines one (exceptionally also none) of the images B as a projection image B. For it looks firstly in step S15 for the particular image among the selected images B, in which the size of the difference between the phase information $\phi$ and the reference phase $\phi^*$ is minimal. It then checks whether this difference is less than the phase boundary $\delta\phi$. If the evaluation facility 8 can determine such an image B, it defines this image B in step S15 as the projection image B for the respective iteration i. If it cannot determine any such image B, it notes this correspondingly.

In step S16 the evaluation facility 8 checks whether the index i has already reached its maximum value. If this is not the case, the evaluation facility 8 increments the index i in step S17 and goes back to step S14. Otherwise, the definition of the projection images B is terminated.

This procedure, which is an integral part of the invention there, ensures that the pixel values of pixels corresponding to one another 9 in the projection images B are also defined, where the examination object 3 has moved iteratively during the capturing of the entire series of images B, by at least essentially locationally identical areas of the examination object 3.

In a step S18, the evaluation facility 8 outputs the number of projection images B determined and the number of iterations of the examination object 3 to the user 6 via the display device 16. Said user 6 can thus identify whether they have made a good selection in respect of the reference phase $\phi^*$ and/or the phase boundary $\delta\phi$.

In a step S19, the evaluation facility 8 waits for a user input. If such an input has been made, the evaluation facility 8 checks in a step S20 whether this input was a confirmation by the user 6. If this is the case, the selection of projection images B is completed and the process can continue with the actual image evaluation method.

Otherwise, the evaluation facility 8 checks in a step S21 whether the user 6 has input a request for the reference phase $\phi^*$ and/or the phase boundary $\delta\phi$ to be changed. If this is the case, the evaluation facility 8 goes back to step S12.

Otherwise the user 6 has input a request for one of the projection images B to be displayed. In this case, the evaluation facility 8 receives a corresponding selection from the user 6 in a step S22. In a step S23, it then displays the selected projection image B on the display device 16. It also outputs, together with the selected projection image B, the corresponding phase information $\phi$ of the selected projection image B, the reference phase $\phi^*$, their difference and the phase boundary $\delta\phi$ to the user 6 via the display device 16. It then goes back to step Si9. It would optionally also be possible to display an overall representation of the phase profile and to show the phase information $\phi$ of all the projection images B simultaneously.

For the sake of completeness, it should be mentioned that steps S12 to S23 are only expedient and/or necessary when a selection of projection images B has to be made from the entire series of images B. If, on the other hand, the captured images B are already all suitable a priori, steps S12 to S23 can be omitted.

It should furthermore be mentioned that, as an alternative to the procedure described above in conjunction with FIG. 5, it is also possible to stipulate in advance suitable intervals for the phase information $\phi$ and to determine for each interval the number of possible projection images B. In this case the evaluation facility 8 can output a list or table, based on which the user 6 can identify how many projection images B are available to them and for which phase interval respectively. In this case the user 6 only has to select the phase interval they desire.

When the selection of projection images B from the entire series of images B is completed, the process continues with FIG. 6. Steps S31 and S32 in FIG. 6 correspond on the one hand to step S11 and on the other hand to steps S12 to S23 in FIG. 5. Since step S32 is only optional, as previously mentioned, it is represented in FIG. 6 by dashed lines only.

In a step S33, the evaluation facility 8 receives a sub-area 18 from the user 6. The evaluation facility 8 overlays this sub-area 18 in a step S34 into one of the projection images B and outputs this projection image B together with the marking of the sub-area 18 to the user 6 via the display device 16. This can also be seen from FIG. 3. The sub-area 18 corresponds to the black frame in FIG. 3.

In a step S35 the computer 8 then determines the type of each pixel 9 which lies within the predefined sub-area 18. Type 1 corresponds to the non-perfused part of the surroundings of a vessel. Type 2 corresponds to a vessel and type 3 to the perfused part of the surroundings of a vessel.

In a step S36, the evaluation facility 8 checks for each pixel 9 within the sub-area 18, whether the type 3 was assigned to this pixel 9. If this is the case, the evaluation facility 8 determines an extent of perfusion for the respective pixel 9 in a step S37 and assigns the extent determined to the relevant pixel 9.

The assignment of the respective type and optionally also the extent of perfusion to the individual pixels 9 defines an evaluation image A. Due to the way in which the evaluation image A is generated, each pixel 9 of the evaluation image A corresponds to the corresponding pixels 9 of the projection images B. In particular the evaluation image A is also two-dimensional and comprises a plurality of pixels 9. The evaluation facility 8 outputs the evaluation image A to the user 6 via the display device 16 as part of a step S38.

Steps S35 to S37, which relate to the actual core of the invention of DE 10 2005 039 189.3, will be examined in more detail again later.

FIG. 7 shows an evaluation image A. In accordance with FIG. 7, the evaluation facility 8 has converted the extent of perfusion and also the type to color values based on an assignment rule. The evaluation facility 8 consequently outputs the evaluation image A in the form of a color-coded representation to the user 6 via the display device 16. The evaluation facility 8 can optionally output the assignment rule together with the color-coded representation to the user 6 via the display device 16.

It is possible for the computer 8 to display the entire displayed evaluation image A in a color-coded manner. In the meantime however it is preferred that the computer 8 displays the evaluation image A outside the perfusion area in black/white or as a gray-scale image. In particular the computer 8 can also subdivide the evaluation image A outside the perfusion area into parcels 19 and assign a gray-scale or one of the black/white values to the parcels 19 of the evaluation image A outside the perfusion area.

As an alternative to the representation as shown in FIG. 7, it is also possible, as shown in FIG. 8, to overlay one of the projection images B in the evaluation image A.

As can further be seen from FIG. 7, other data can also be overlaid in the evaluation image A, for example a first threshold value SW1, a limit time GZP, a factor F and further values. The significance of these values will become evident later.

In accordance with FIGS. 7 and 8, only the sub-area 18 is displayed and output. It is however of course also possible to output the entire evaluation image A, over and above the sub-area 18, to the user 6 via the display device 16 and in this case to mark the sub-area 18 correspondingly as in FIG. 3.

In a step S39, the evaluation facility 8 waits for an input from the user 6. When this input has been made, the evaluation facility 8 checks in a step S40 whether the input was a confirmation. If this is the case, in a step S41 the evaluation facility 8 generates a report based on the evaluation image A and assigns the evaluation image A and the report to the projection images B. It then archives at least the projection images B, the evaluation image A and the report as a unit.

Otherwise the evaluation facility 8 checks in a step S42 whether the input was an instruction to reject the evaluation image A. In this case, the image evaluation method is simply quit without further ado, without saving the report.

Otherwise the evaluation facility 8 checks in a step S43 whether the criteria for defining the type and/or the extent of perfusion are to be changed. If this is the case, in a step S44 the evaluation facility 8 receives new criteria and goes back to step S35.

Even if the criteria are not to be changed, the user 6 may have selected only a pixel 9 or a group of pixels 9. In this case, in a step S45 the evaluation facility 8 receives a corresponding selection of a pixel 9 or of a group of pixels. In a step S46 it determines for the selected pixel 9 or for the selected group of pixels the temporal profile of the mean value of the corresponding areas of the projection images B, by means of which it determined the extent of perfusion for the selected pixel 9 or the selected group of pixels, and outputs this profile to the user 6 via the display device 16.

FIG. 9 shows a possible implementation of steps S35 to S37 from FIG. 6.

In accordance with FIG. 9, in a step S51 the evaluation facility 8 subdivides the projection images B into two-dimensional parcels 19. The subdivision of parcels 19 can be seen for example from FIG. 3. According to FIG. 3 the parcels are rectangular. This is the simplest type of subdivision into parcels 19. However other parcel forms are also possible, in particular equilateral triangles and regular hexagons.

The size of the parcels 19 is in principle freely selectable. They must be two-dimensional. Furthermore they should comprise so many pixels 9 that, when a mean value is formed, the noise tends to be averaged out and motion artifacts are negligible, at least as a general rule. On the other hand the resolution should be sufficiently good. It was determined in trials that the parcels 19 should preferably contain between about 60 and around 1,000 pixels 9, which in the case of rectangular parcels 19 may correspond to an edge length from for example 8×8 pixels to for example 32×32 pixels.

In steps S52 and S53, the evaluation facility 8 sets the serial indices i, j to the value one. The index i runs sequentially through each parcel 19 of the two-dimensional arrangement of parcels 19 as shown in FIG. 3. The index j runs sequentially through the projection images B.

In a step S54 the evaluation facility 8 determines the—weighted or unweighted—mean value M(j) of the pixel values of the parcel 19 defined by the index i in the projection image B defined by the index j.

In a step S55 the evaluation facility 8 checks whether the index j has already reached its maximum value. If this is not the case, the evaluation facility 8 increments the index j in a step S56 and goes back to step S54, in order to determine the next mean value M(j).

When all the mean values M0) are determined for a specific parcel 19, in a step S57 the evaluation facility 8 uses these mean values M(j) to define the type of the respective parcel 19 and assigns the determined type to a parcel 19 of the evaluation image A—see FIG. 7. The parcels 19 of the evaluation image A correspond 1:1 to the parcels 19 of the projection images B.

The evaluation facility 8 then checks in a step S58 whether the type determined corresponds to type 3, i.e. to the type "perfused part of the surroundings". If this is the case, in a step S59 the evaluation facility 8 uses the same mean values M(j) to define the extent of perfusion for this parcel 19 and assigns it likewise to the corresponding parcel 19 of the evaluation image A.

The evaluation facility 8 then checks in a step S60 whether it has already carried out step S53 to S59 for all the parcels 19. If this is not the case, it increments the index i in a step S61 and goes back to step S53. Otherwise the determination and assignment of the type and also of the extent of perfusion according to the doctrine of DE 10 2005 039 189.3 is terminated.

According to the doctrine of DE 10 2005 039 189.3 modifications of the method described in conjunction with FIG. 9 are possible. Thus for example the order of the indices i, j in particular can be swapped. In this case, a number of modified projection images B' are determined. Each of these modified projection images B' has a uniform value per parcel 19, namely the mean value M(j) determined in step S54. An example of a projection image B' modified in this way is shown in FIG. 10.

The procedure according to the invention described above achieves in particular the following features:

The evaluation facility 8 carries out the assignment of the type based on the temporal profile of the pixel values of the projection images B.

The evaluation facility 8 carries out the assignment of the type and of the extent of perfusion based on the temporal profile of the pixel values of those pixels 9 of the projection images B, which lie in a two-dimensional evaluation core 19 of the projection images B defined by the respective pixel 9 of the evaluation image A. For the evaluation core 19 corresponds to the respective parcel 19.

For the same reason, the evaluation facility 8 also carries out the assignment of type and extent for all the pixels 9 of a parcel 19 in a uniform manner.

Furthermore the same parcels 19 are used for determining type and for determining extent.

FIG. 7 and also FIG. 8 show the outcome of the assignment.

As an alternative to the parcel-by-parcel assignment of type and extent of perfusion of the individual pixels 9 of the evaluation image A, it would also be possible for the evaluation facility 8 to define a specific two-dimensional evaluation core in the projection images B for each pixel 9 of the evaluation image A, the respective pixel 9 of the evaluation image A being arranged in the center of the respective evaluation core. Even then a fully analogous procedure is possible. However a considerably greater computation outlay would be required for this and it would not be matched by any significant gain in accuracy.

If a lot of contrast medium is present in the examination object 3, only a relatively low level of transmission takes place. This produces a relatively low level of brightness (tending toward black) in the projection images B. Conversely, if only a small amount of contrast medium is present in the examination object 3, a higher level of transmission takes place, as a result of which greater brightness is produced in the projection images B (tending toward white). As a rule, when the projection images B are digitized, black is assigned the pixel value zero, white the maximum possible pixel value e.g. $2^8-1=255$. The converse of the conventional procedure is followed below. Thus white is assigned the pixel value zero and black the maximum possible pixel value. This assignment facilitates understanding of the remarks below. The assignment of zero to white and maximum value to black is however not required in principle.

It will now be described in conjunction with FIGS. 11 to 13 how the evaluation facility 8 determines the type of the individual parcels 19. For this purpose the evaluation facility 8 needs two decision criteria, namely the first threshold value SW1 and the limit time GZP.

If in a specific parcel 19 in all the projection images B the difference between the mean values M(j) determined and the corresponding mean value M(1) of the first projection image B reaches as a maximum the threshold value SW1, the type "background" or "non-perfused part of the surroundings" is assigned to the respective parcel 19. FIG. 11 shows a typical example of such a mean-value profile.

The first threshold value SW1 can be predefined in a fixed manner. It can for example amount to 5 or 10% of the maximum control range. It can also be defined relative to the mean value M(1) of the respective parcels 19 of the first projection image B. It can amount for example to 10 or 20% of the mean value M(1). The first threshold value SWI is preferably a function of both an input of the user 6 and the mean value M(1) of the corresponding parcel 19 of the temporally first projection image B. This can be achieved in particular in that the user 6 predefines the factor F for the evaluation facility 8 in accordance with a step S71 shown in FIG. 14 and in a step S72 the evaluation facility 8 then defines the first threshold value SW1 for the respective parcel 19 as a product of the factor F and of the mean value M(1) of the respective parcel 19.

If the type of a parcel 19 does not correspond to the type "background", the parcel 19 must either be assigned the type "vessel" or the type "perfused part of the surroundings". The limit time GZP serves to distinguish between these two types. If the first threshold value SW1 is exceeded for the first time before the limit time GZP, the type "vessel" is assigned to a parcel 19, otherwise the type "perfused part of the surroundings" is assigned.

The limit time GZP can also be predefined in a fixed manner for the evaluation facility 8. The limit time GZP also preferably depends on an input by the user 6. Steps S73 to S75, as shown in FIG. 14, are available for this purpose. In step S73 the evaluation facility 8 receives the limit time GZP from the user 6. In step S74 the evaluation facility 8 determines the particular projection image B which lies closest in time to the limit time GZP. It outputs this projection image B as part of step S74 to the user 6 via the display device 16. In step S75 the evaluation facility 8 checks whether the user 6 confirms the limit time GZP or whether said user 6 desires a new predefinition. Accordingly the method either returns to step S73 or proceeds with a step S76, in which the type assignment takes place for the individual parcels 19.

FIGS. 12 and 13 each show an example of a temporal profile for a parcel 19 of the type "vessel" and "perfused part of the surroundings".

In accordance with step S76, the following type assignment takes place: If it is true for all possible indices j that the amount of the difference between the mean value M(j) of the projection image B(j) and the mean value M(1) of the temporally first projection image B(1) is less than the first threshold value SW1, type 1 (background) is assigned to the corresponding parcel 19. If a value for the index j exists, for which the above-mentioned difference exceeds the first threshold value SW1 and the index j corresponds to a capture time t(j), which lies before the limit time GZP, type 2 (vessel) is assigned to the relevant parcel 19. Otherwise type 3 (perfused part of the surroundings) is assigned to the relevant parcel 19.

In a step S77 the evaluation facility 8 checks whether the type determined is type 3. Only if this is the case are steps S78 to S80 carried out. Otherwise steps S78 to S80 are skipped.

In step S78 the evaluation facility 8 carries out a calculation of the extent of perfusion. This calculation can be done in many different ways. This is explained in more detail below in conjunction with FIG. 15. It should be mentioned in advance that in the simplest case only two or three values are distinguished for the extent of perfusion, that is only high and low or high, moderate and low. Finer subdivisions are however also possible.

In accordance with FIG. 15, the temporal profile of the mean value M in a parcel 19 of type 3 exceeds the first threshold value SW1 for the first time at a time T1. At a time T2 the mean value M reaches 90% of its maximum Mmax for example. At a time T3 the mean value M reaches its maximum Mmax. At a time T4 the mean value M drops back to 90% of its maximum Mmax for example. At a time T5 the mean value M drops back to below the first threshold value SW1. The numerical value 90% is given only by way of example. A different percentage could of course also be used. Also a correction by a base value M0 can optionally be carried out. The base value M0 is defined here for the parcel 19 under consideration as the mean value of the mean values M before the limit time GZP or before the time T1.

In addition to the above-mentioned times T1 to T5, an auxiliary time T6 can be defined, in which the mean value M exceeds a second threshold value SW2. Here the second threshold value SW2 preferably corresponds to what is known as FWHM (FWHM=full width at half maximum).

As regards the extent of perfusion, it is possible for the evaluation facility 8 to determine this from one of these variables or from a number of these variables. Several possible evaluations are indicated in DE 10 2005 039 189.3.

In step S79 the evaluation facility 8 checks whether the time period T6 exceeds a minimum time Tmin. If this is not the case, the time period T6 is extremely short. An example of such a profile is shown in FIG. 16. This points with high probability to what is known as an artifact. In this case the evaluation facility 8 skips to step S80. In step S80 it ensures that the corresponding projection image B is ignored with regard to the parcel 19 currently being processed. In the simplest case the respective projection image B (restricted of course to the respective parcel 19) is omitted. The evaluation facility 8 preferably makes a replacement. It replaces the parcel 19 being processed with the corresponding parcel 19 of the projection image B immediately preceding in time, of the projection image B immediately succeeding in time or with an interpolation of the corresponding parcels 19 of the projection images B immediately preceding in time and immediately succeeding in time. After step S80 has been executed, the evaluation facility 8 goes back to step S78.

The image evaluation method of DE 10 2005 039 189.3, as described above, can optionally be refined as required. For example it is possible, after the extent of perfusion has been determined parcel by parcel, to carry out a finer determination. This is described in more detail below in conjunction with FIG. 17.

As shown in FIG. 17, the evaluation facility 8 selects a parcel 19 in a step S91. In a step S92 the evaluation facility 8 checks whether type 3 is assigned to the selected parcel 19. Only if this is the case is the move made to a step S93. In step S93 the evaluation facility 8 calculates the logical auxiliary variable OK. OK assumes the value "true" if, and only if, the selected parcel 19 is completely surrounded by parcels 19 to which type 3 is also assigned.

The value of the logical auxiliary variable OK is checked in step S94. Depending on the result of the check, steps S95 and S96 are then executed. In step S95 the selected parcel 19 is subdivided, for example into 2×2=4 sub-parcels. In step S96 the evaluation facility 8 carries out a determination and assignment of the extent of perfusion again for each sub-parcel.

In step S97 the evaluation facility 8 checks whether it has already carried out steps S92 to S96 for all the parcels 19. If this is not the case, it moves on to a step S98 by selecting a different, previously not yet selected, parcel 19. From step S98 it goes back to step S92.

The procedure shown in FIG. 17 can of course be modified. Thus for example step S95 can be brought forward before step S91 so that it is carried out for all the parcels 19. Steps S91 to S94 and S97 and S98 are then carried out respectively with the sub-parcels. Irrespective of whether the one or the other procedure is adopted however, the evaluation facility 8 determines the extent of perfusion again only for those pixels 9 of the evaluation image A, to which the type "perfused part of the surroundings" is assigned and which are surrounded within a predetermined minimum distance (here a parcel 19 or a sub-parcel) exclusively by pixels 9 to which the type "perfused part of the surroundings" is also assigned.

In the context of the above explanation it was assumed that the recording parameters of the recording arrangement 1, including the operating parameters of the radiation source 4, were kept constant during the capturing of the images B. If this prerequisite is not satisfied, brightness fluctuations can occur in the captured images B, which can impair the evaluation and in extreme cases even render it impossible. Within the scope of the doctrine of DE 10 2005 039 189.3, there is therefore provision for carrying out corresponding corrections, so that an evaluation can nevertheless take place. These corrections take place before step S35 or after step S44 in FIG. 6. They are described in more detail below in conjunction with FIG. 18.

In accordance with FIG. 18, in a step S101 a reference area 20 of the projection images B is firstly defined. In the simplest case the reference area 20 is defined by means of a corresponding user input. The evaluation facility 8 then overlays the reference area 20 into one of the projection images B in a step S102. This can be seen for example in FIG. 3.

Next, in a step S103, the evaluation facility 8 defines one of the projection images B as a reference image B. It is in principle random, which of the projection images B is defined as the reference image B. As a rule, the first or the last of the projection images B is defined as the reference image B.

In a step S104, the evaluation facility 8 selects one of the projection images B.

In a step S105 the evaluation facility 8 compares the selected projection image B with the reference image B. The comparison is carried out only within the reference areas 20 that correspond to one another. In a step S106 the evaluation facility 8 defines a transformation of the pixel values of the selected projection image B based on the comparison. The transformation is defined such that the mean value of the pixels 9 of the reference area 20 of the transformed projection image B on the one hand and the mean value of the pixels 9 of the reference image B on the other hand have a predetermined functional relationship to one another. The functional relationship can consist in particular of the fact that the mean value of the pixels 9 of the reference area 20 of the transformed projection image B is equal to the mean value of the pixels 9 of the reference image B. The transformation can alternatively be linear or non-linear.

In accordance with the transformation specified in step S106, in a step S107 the evaluation facility 8 transforms all the pixels 9 of the selected projection image B, in other words both the pixels 9 inside the reference area 20 and the pixels 9 outside the reference area 20.

In a step S108, the evaluation facility 8 checks whether it has already carried out steps S104 to S107 for all the projection images B. If this is not yet the case, it moves on first to a step S109 in which it selects another of the projection images B. It then goes back to step S105. Otherwise the transformation of the projection images B is terminated.

As an alternative to the user 6 predefining the reference area 20, it is possible for the evaluation facility 8 to determine the reference area 20 automatically. For example the evaluation facility 8 can determine the reference area 20 from the pixels 9 of the evaluation image A, to which it has assigned the type "non-perfused part of the surroundings", in other words type 1. Parcels 19 which lie outside the exposure area are not taken into account here. This is described in more detail in DE 10 2005 039 189.3.

In contrast to the known prior art, with DE 10 2005 039 189.3 it is no longer necessary for the user to predefine which area of the projection images corresponds to the myocardium. Rather the type assignment can take place from the projection images themselves.

The image evaluation method in DE 10 2005 039 189.3 is universally applicable. It is also applicable in particular therefore, when the examination object is not moving. An example of such an examination object is the human brain, in which the same blood supply problems can occur as in the human heart. When they occur acutely, these blood supply problems are known as a stroke.

As already mentioned, the present invention is based on this doctrine. An understanding of it is therefore assumed below. This doctrine is also an integral part of the present invention, unless the statements below contain information to the contrary.

An object of the present invention is to create an image evaluation method, which allows an image evaluation, which is optimized compared with the image evaluation described in DE 10 2005 039 189.3.

The object is achieved by an image evaluation method with the features of an independent claim.

According to the invention the object is thus achieved by means of the following features:

A computer assigns a two-dimensional evaluation core that is uniform for all corresponding pixels to pixels of projection images that correspond to one another at least in a sub-area of the projection images that is uniform for the projection images.

The computer determines at least one characteristic value for each pixel within each projection image based on the evaluation core assigned to the respective pixel and assigns this value to the relevant pixel.

The computer determines parameters of at least one function of time based on the temporal profile of the characteristic values assigned to corresponding pixels, so that any deviation between the function of time parameterized with the parameters and the temporal profile of the characteristic values assigned to corresponding pixels is minimized.

The computer uses the parameters to determine a type and/or an extent and assigns the type and/or extent to a pixel of a two-dimensional evaluation image corresponding to the pixels of the projection images.

The type is characteristic of whether the respective pixel of the evaluation image corresponds to a vessel of a vascular system, a perfused part of the surroundings of a vessel of the vascular system (perfusion area) or a non-perfused part of the surroundings of a vessel of the vascular system (background). The extent is characteristic of the extent of perfusion (degree of perfusion).

The computer outputs at least the sub-area of the evaluation image to the user via a display device.

In a corresponding manner the object for the data medium or computer is achieved in that a computer program for carrying out such an image evaluation method is stored on the data medium or such a computer program is filed in the mass memory of the computer, in such a manner that the computer executes said image evaluation method after the computer program has been called.

The first two and last two of the aforementioned features indented with a dash above are already described in DE 10 2005 039 189.3. The two middle features indented with a dash are however novel in respect of DE 10 2005 039 189.3.

The computer preferably assigns the maximum of the pixel values occurring in the evaluation core assigned to the respective pixel to the pixels as a characteristic value. In this case it is possible for the computer to use the temporal profile of the maximum to define parameters of a maximum function, so that any deviation between the maximum function parameterized with the parameters and the temporal profile of the maximum is minimized. It is also possible in this case for the computer to use the parameters of the maximum function to determine whether it assigns the type "vessel" to the corresponding pixel of the evaluation image.

This procedure is novel in respect of DE 10 2005 039 189.3, as only mean values are processed there.

Alternatively or additionally it is possible for the computer to assign the mean value of the pixel values occurring in the evaluation core assigned to the respective pixel to the pixels as a characteristic value. This procedure is known from the start from DE 10 2005 039 189.3.

The last-described procedure is possible as an alternative to determining the maxima as characteristic values. It is preferably carried out as an addition.

If the computer 8 determines the mean values as characteristic values, it is possible for the computer to use the temporal profile of the mean value to define parameters of a mean value function, so that any deviation between the mean value function parameterized with the parameters and the temporal profile of the mean value is minimized. In this case the computer can use the parameters of the mean value function to determine whether it assigns the type "perfusion area" or the type "background" to the corresponding pixel of the evaluation image and/or can use the parameters of the mean value function to determine which degree of perfusion it assigns to the corresponding pixel.

The mode of operation in principle described above already provides very good results. It can be even further improved using the procedures described below.

It is thus for example possible for the computer to determine a histogram of the pixel values occurring in the respective evaluation core to define the mean value and to determine said mean value using the histogram. In particular the computer can use the histogram to determine statistic variables relating to the distribution of the pixel values and to decide based on the statistic variables, which of the pixel values it takes into account when determining the mean value.

The parameterizable function can be adapted to the overall anticipated blush profile. In this case the at least one parameterizable function increases from an initial value to a maximum value and then decreases from the maximum value to a final value, as time progresses. For example the function can have the form $$y = K1 \cdot (1 + e^{-a(t-T')})^{-1} \cdot (1 + e^{b(t-T'')})^{-1} + K2$$

where y is the function value, t the time and K1, K2, a, b, T' and T" are the parameters of the function.

It is possible for the size of the evaluation core to be independent of location. However the size of the evaluation core is preferably a function of location. For example in the outer region, where no or only a small amount of image information is expected, a large evaluation core can be established with a smaller evaluation core in the inner area.

The size of the evaluation core for a specific pixel can be determined beforehand. However the computer preferably determines the size of the evaluation core iteratively based on the type assigned to the pixels, at least for some of the pixels.

It is currently preferable for the computer to subdivide the projection images and the evaluation image into parcels, for the computer to carry out the type and/or extent assignment parcel by parcel and for the evaluation core to correspond to the respective parcel.

In particular if the iterative determination of the size of the evaluation core and the subdivision of the images into parcels are combined, it is possible for the computer to subdivide parcels, to which it has assigned the type "vessel" in one of the iterations, into sub-parcels and to carry out an iteration again, if the relevant parcel is surrounded in an angle range, which is larger than a first minimum angle range, by parcels, to which the computer did not assign the type "vessel" in the first-mentioned iteration, and the parcel is larger than a minimum size.

It is possible for the computer to retain the sub-parcels as such. However it is preferable for the computer to combine sub-parcels, to which it does not assign the type "vessel" in the new iteration, with a parcel adjacent to the relevant sub-parcel, to which the type "vessel" is also not assigned, to form an overall parcel. This measure can reduce computation outlay.

Computation outlay can be further reduced, if the computer combines adjacent parcels of the same type to form an overall parcel. This is particularly so, where parcel combination is carried out for parcels of the type "perfusion area".

It is possible for the computer to change the type to "background" for parcels, to which it assigned the type "perfusion area", if the relevant parcel is surrounded in an angle range, which is larger than a second minimum angle range, by parcels, to which the computer has assigned the type "background". It is possible in particular to eliminate outliers with this procedure.

It is possible for the computer always to carry out the type change, when the last-mentioned condition is satisfied. It is alternatively also possible for the computer only to carry out the type change, when the relevant parcel is surrounded exclusively by parcels of the type "background" and/or the characteristic values of the relevant parcel satisfy a change condition.

The evaluation of the projection images can be further optimized, if the computer determines internally related areas of the evaluation image, in which it has assigned exclusively the type "perfusion area" to the parcels and defines the size of the parcels within the respective area as a function of the size of the respective area. In particular it is possible to select the parcels to be even smaller, the smaller the internally related area.

It is possible for the computer to carry out a vessel segmentation for each projection image based on the pixel values of the respective projection image and to take into account the vessels identified based on the vessel segmentation during the type assignment. This procedure allows more defined separation of the vessels of the vascular system from the remainder of the image.

For example the computer can use the vessels identified in the projection images to determine the vascular system and to take the vascular system as a whole into account during the type assignment.

The evaluation of the projection images is on the one hand particularly simple and on the other hand particularly true to reality, if the computer uses the parameters to determine a characteristic input time for inputting the contrast medium into the corresponding evaluation core for a pixel under consideration and a characteristic washout time for washing the contrast medium out from the corresponding evaluation core and determines the degree of perfusion based on the input and washout times.

The computation time for the required image evaluation can be reduced, if the computer only assigns the type "vessel" to a pixel of the evaluation image, if the parameterized function of time demonstrates a predefined minimum increase before a limit time, the computer defines the parameters of the function exclusively based on the characteristic values of the pixels of the projection images, which are before the limit time in time, and the projection images, which are as a maximum a predefined limit after the limit time in time, and carries out assignment of the type "vessel" based on the parameters thus defined.

The evaluation of the projection images can be even further optimized, if the computer uses at least two different parameterizable functions to determine the individual types and/or the degree of perfusion.

BRIEF DESCRIPTION OF THE DRAWINGS

Further advantages and details will emerge from the description which follows of exemplary embodiments in conjunction with the drawings, in which in schematic representation:

FIG. 1 shows a block diagram of a recording arrangement, a control computer and an evaluation facility,
FIG. 2 shows a flow diagram,
FIG. 8 shows the evaluation image from FIG. 7 with an overlaid projection image,
FIG2 24 and 25 show flow diagrams,
FIG. 27 shows a flow diagram,
FIGS. 29 and 30 show flow diagrams.

DETAILED DESCRIPTION OF INVENTION

Figure 3:
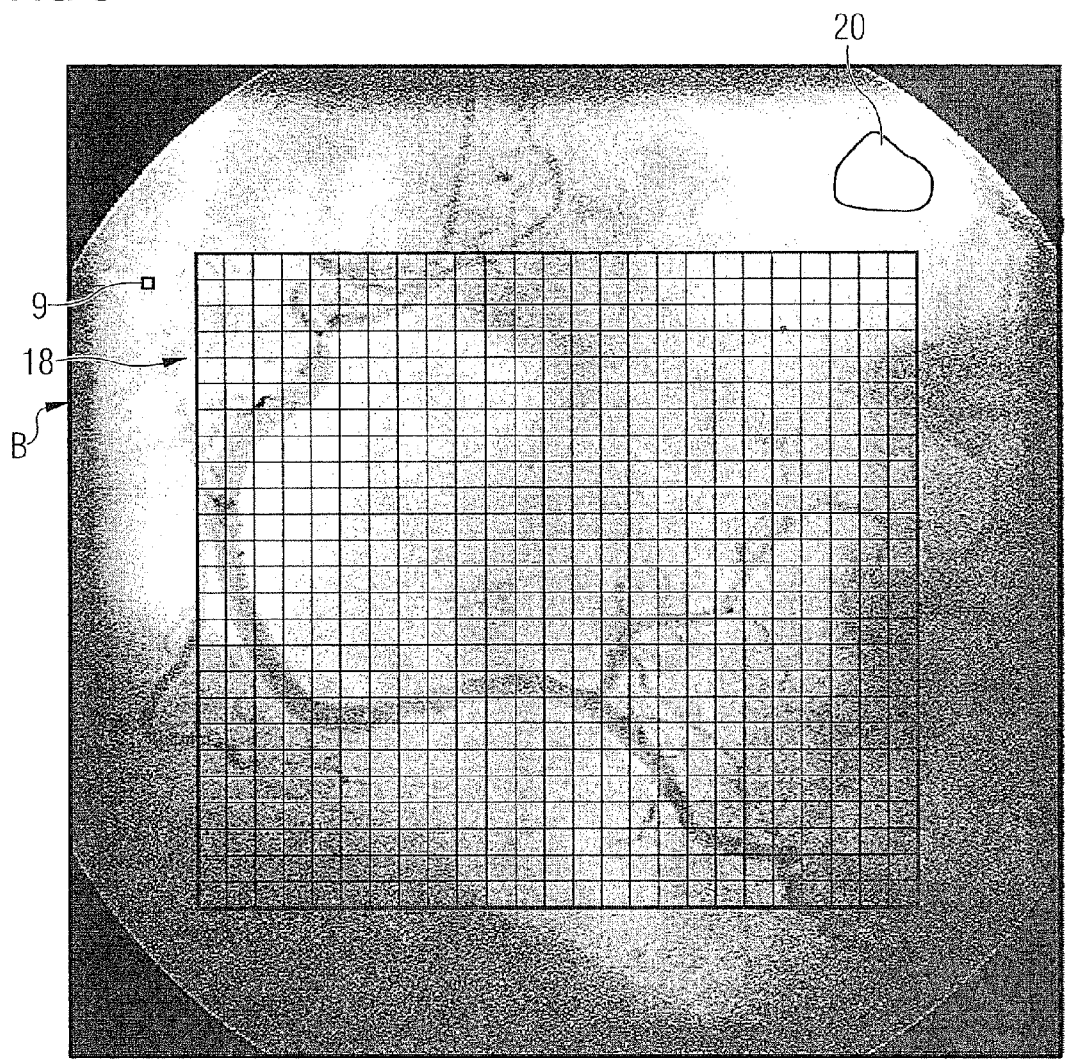
FIG. 3 shows an example of a projection image.
Figure 4:
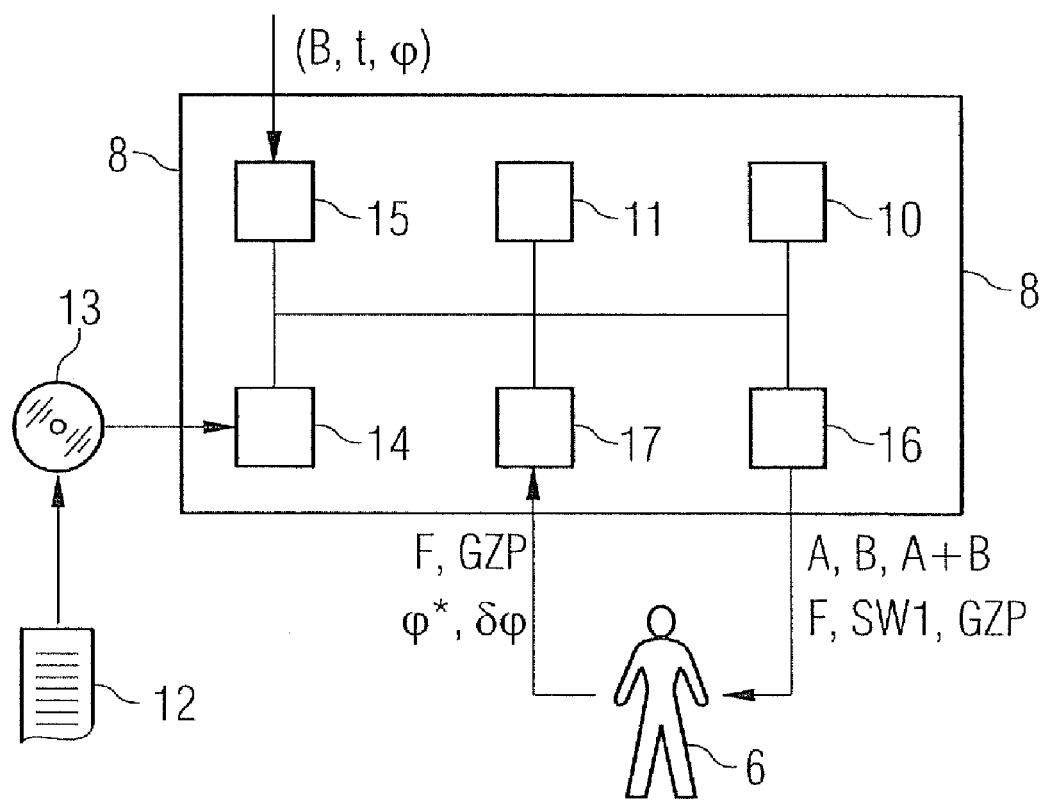
FIG. 4 shows a block diagram of an evaluation facility.
Figure 5:
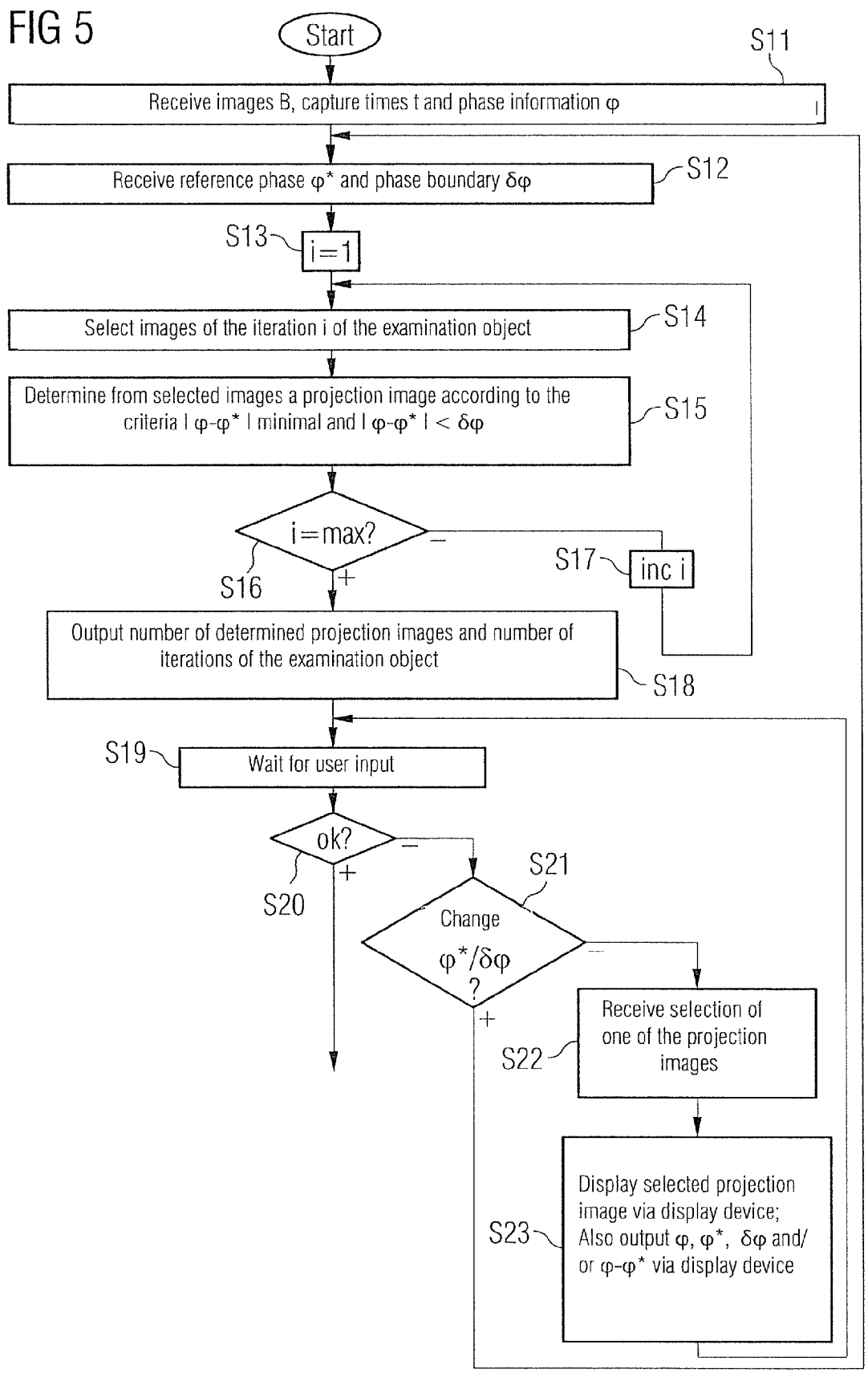
FIGS. 5 and 6 show flow diagrams.

Large sections of the present invention correspond to the procedure described in DE 10 2005 039 189.3. The above comments relating to FIGS. 1 to 8 also apply within the scope of the present invention. Thus for example the present invention relates not only to an image evaluation method as such but also—see also FIG. 4—to a data medium 13 with a computer program 12 stored on the data medium 13, to carry out an inventive image evaluation method. It also relates—see also FIG. 4 again—in addition to the image evaluation method to a computer 8 with a mass memory 11, in which a computer program 12 is filed, so that the computer 12 executes an evaluation method of this type after the computer program 12 has been called.

Figure 6:
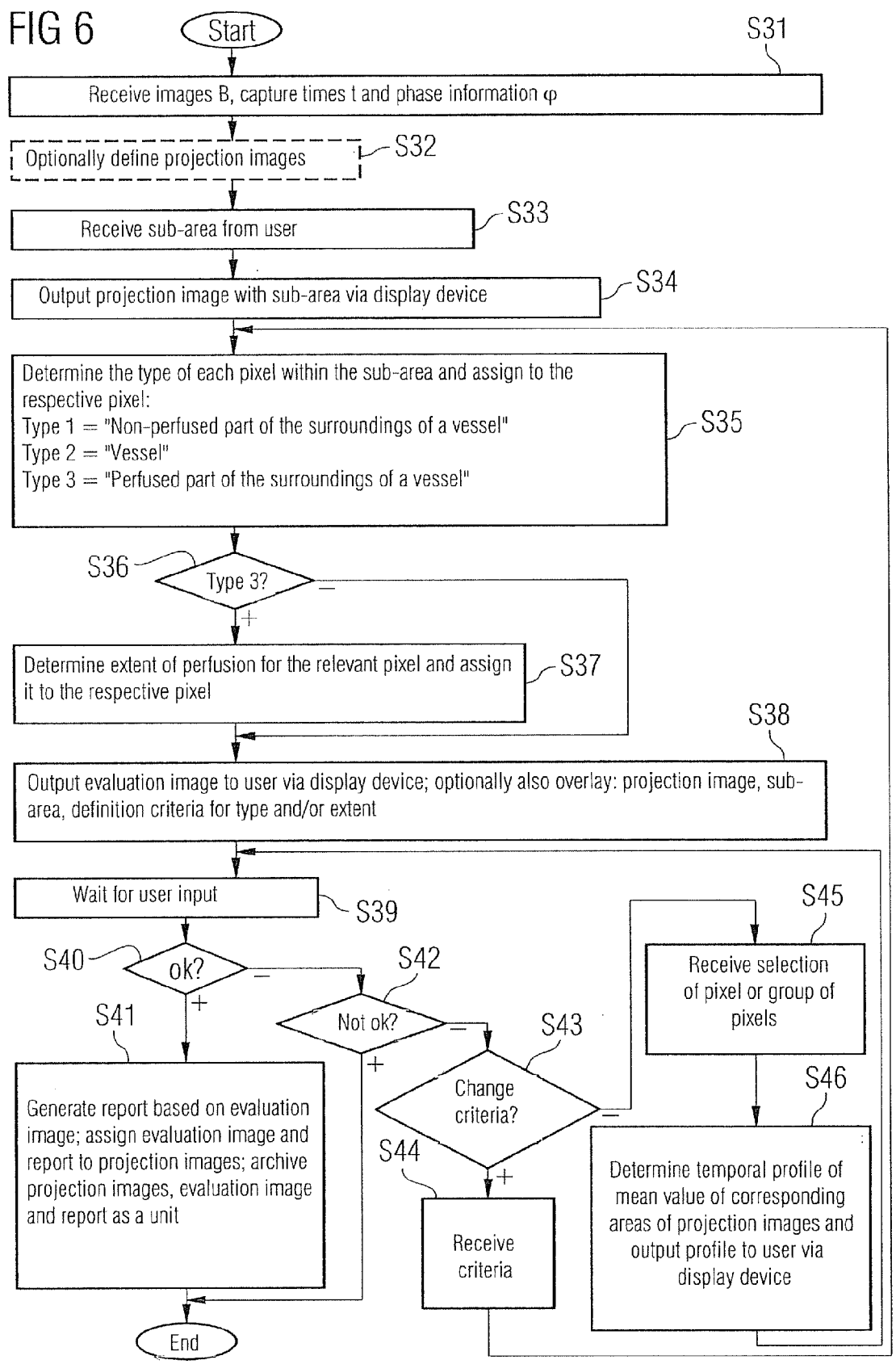
Figure 7:
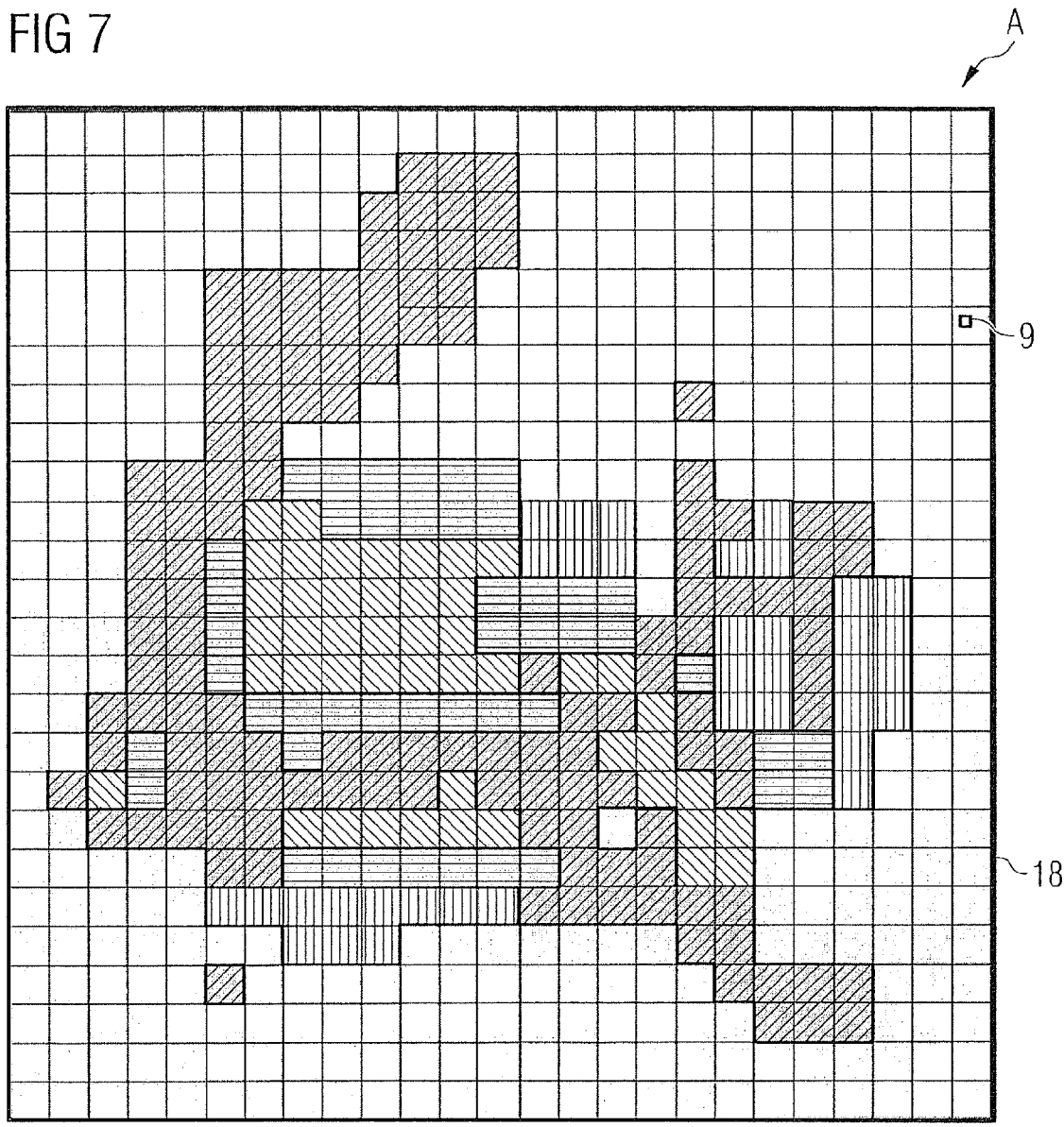
FIG. 7 shows an evaluation image.
Figure 9:
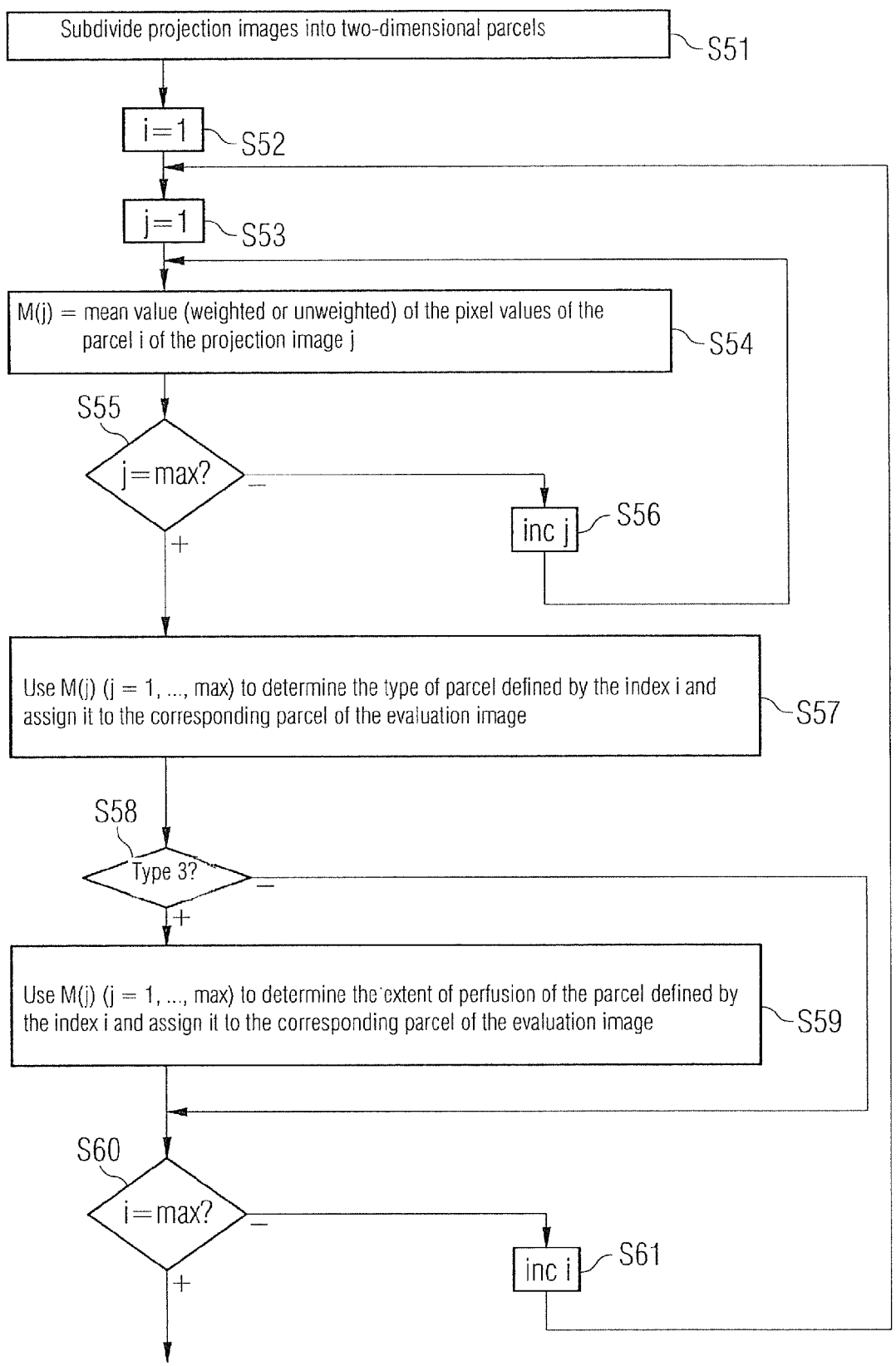
FIG. 9 shows a flow diagram.
Figure 10:
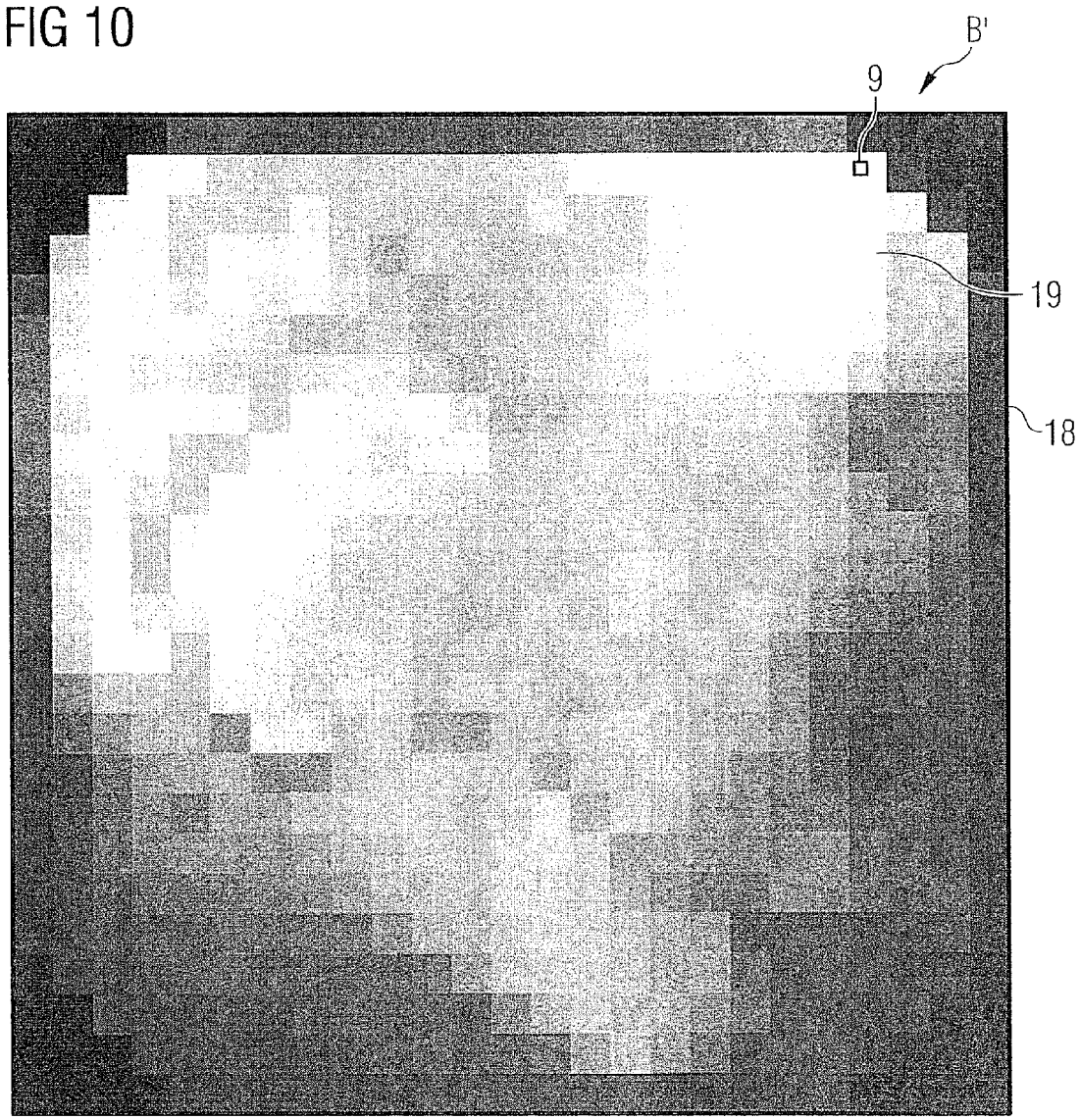
FIG. 10 shows an intermediate image derived from a projection image.
Figure 11:
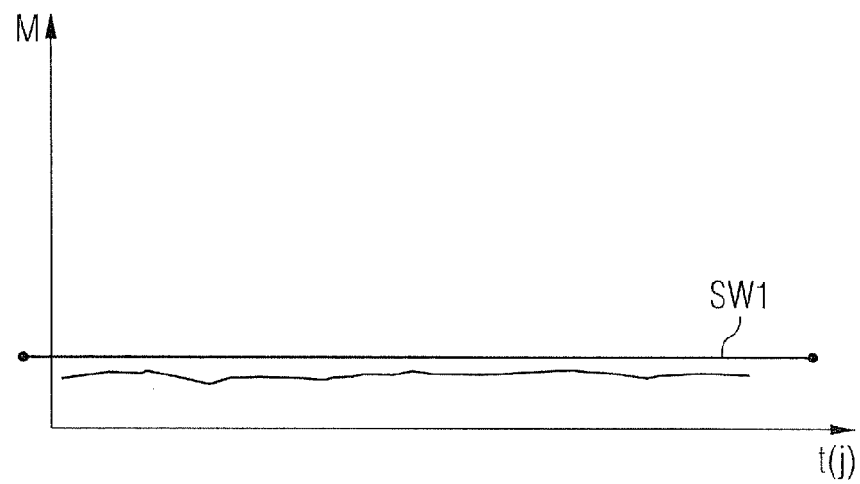
FIGS. 11 to 13 show temporal profiles of mean values.
Figure 12:
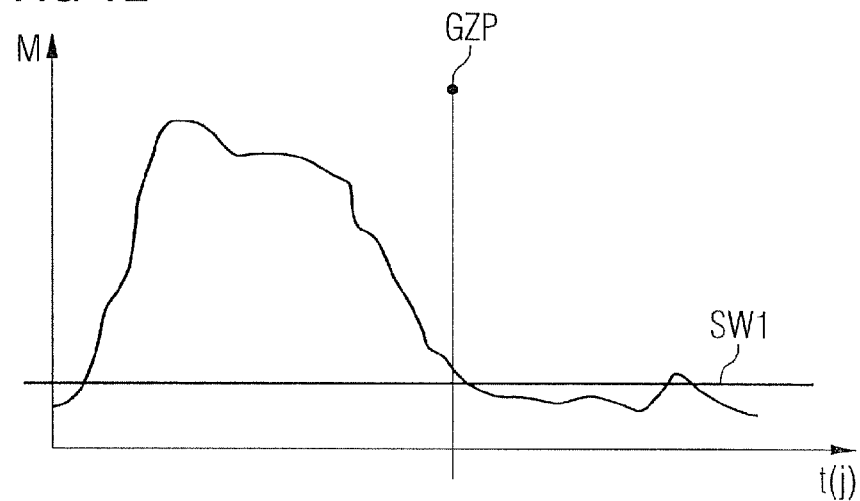
Figure 13:
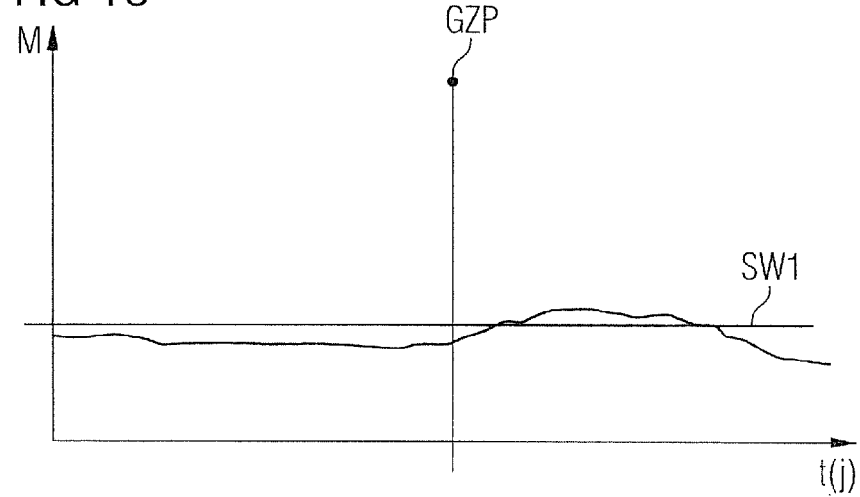
Figure 14:
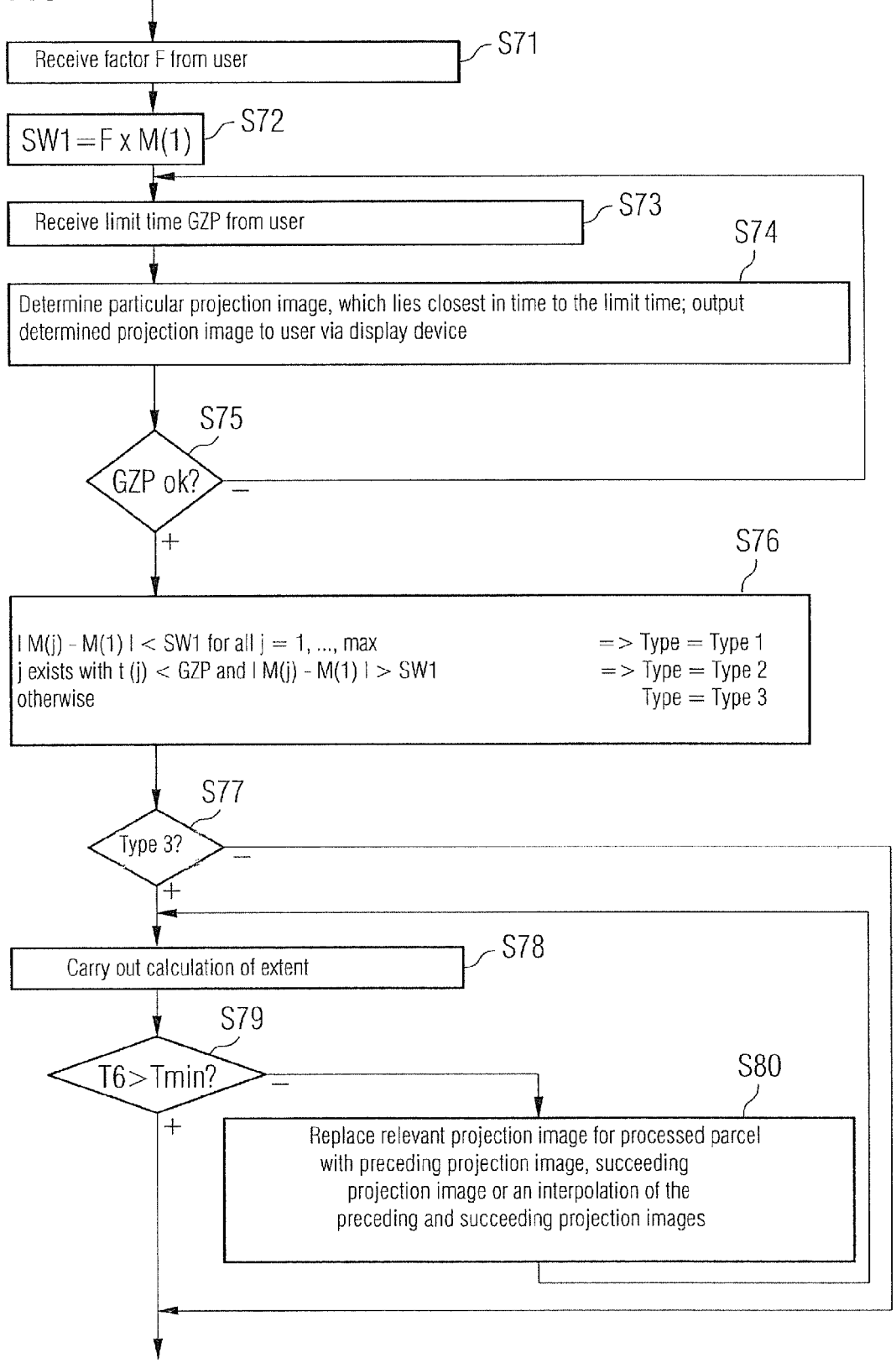
FIG. 14 shows a flow diagram.
Figure 15:
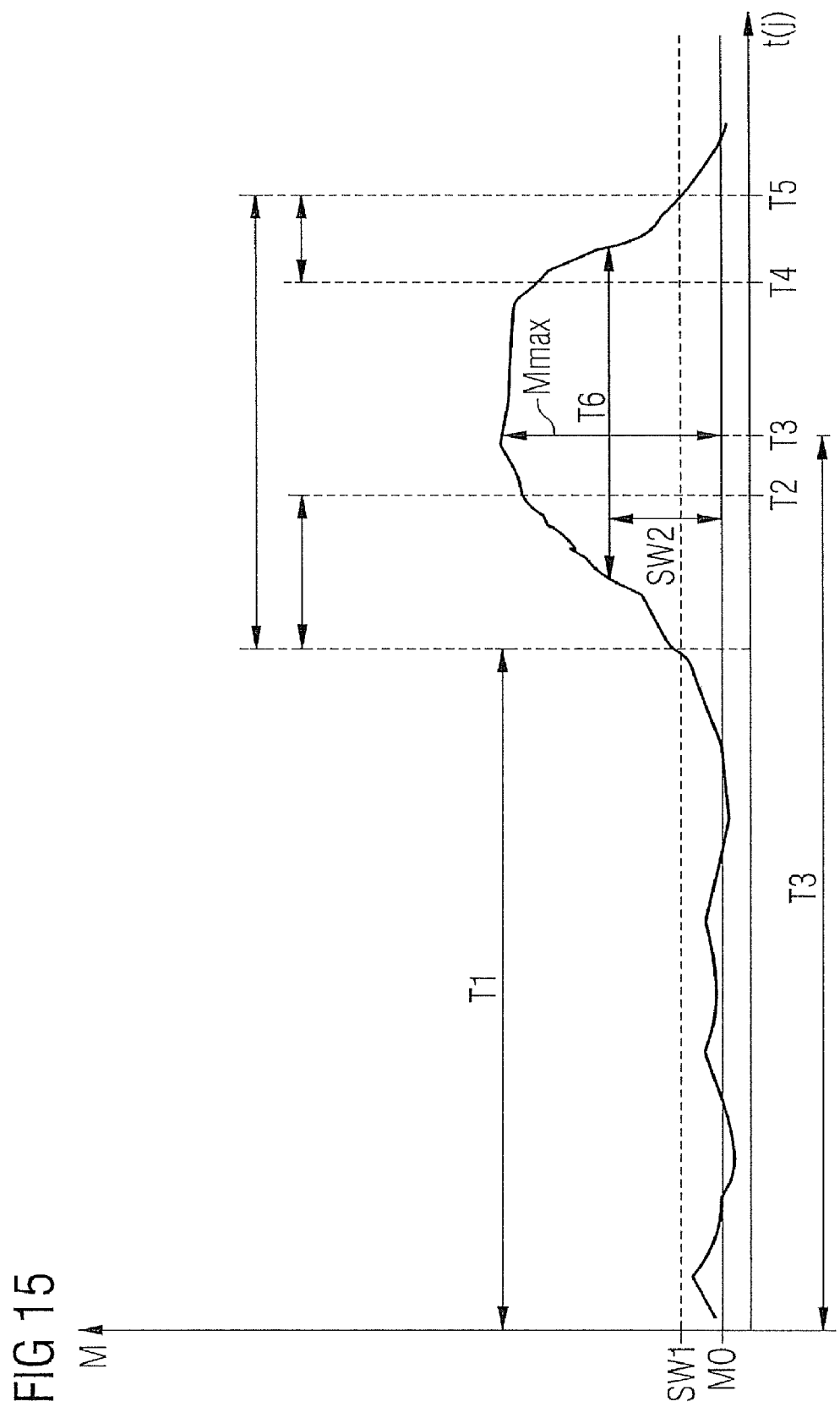
FIG. 15 shows a temporal profile of a mean value.
Figure 16:
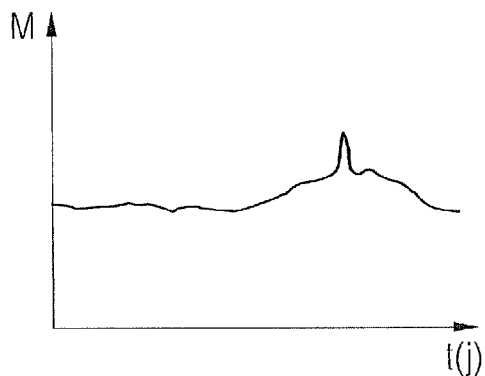
FIG. 16 shows a further temporal profile of a mean value.
Figure 17:
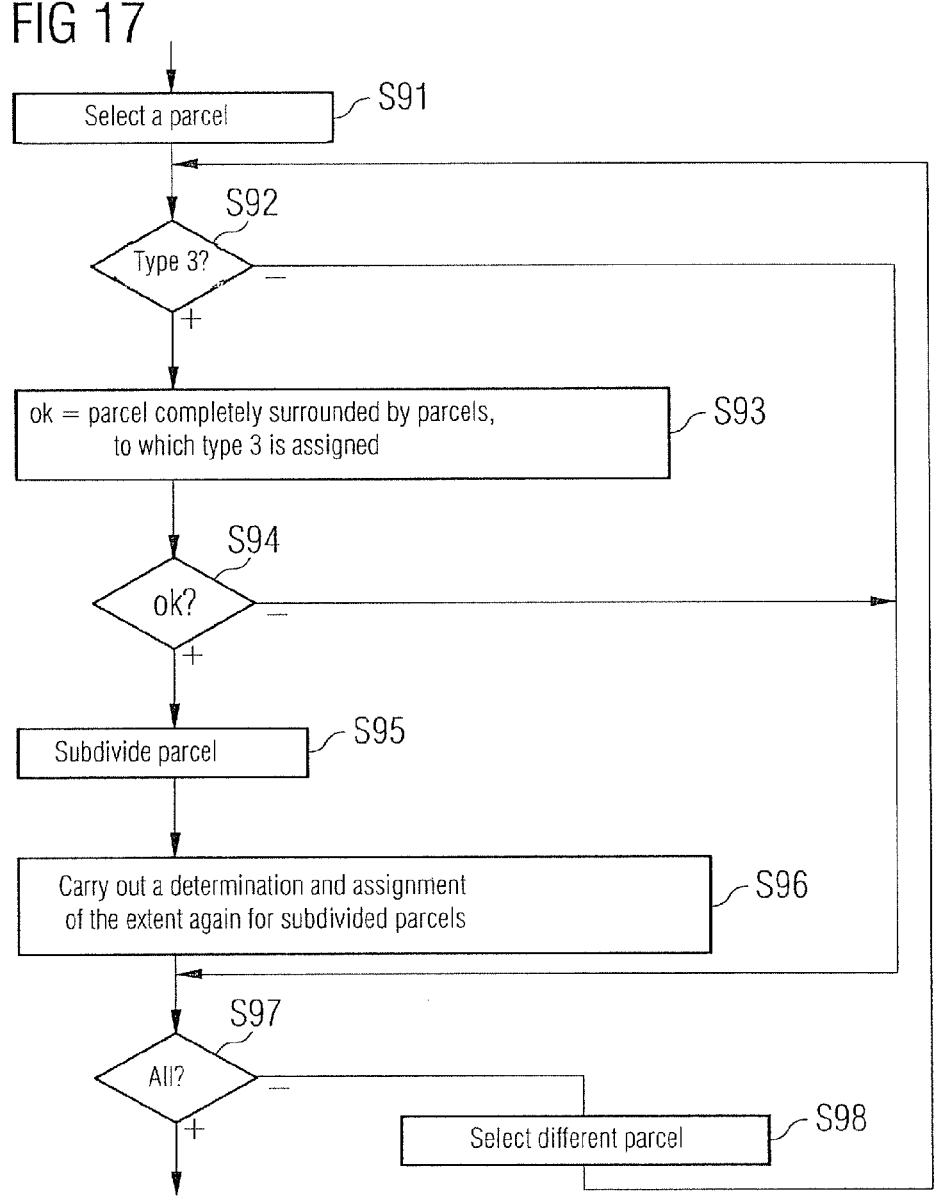
FIGS. 17 to 19 show flow diagrams.
Figure 18:
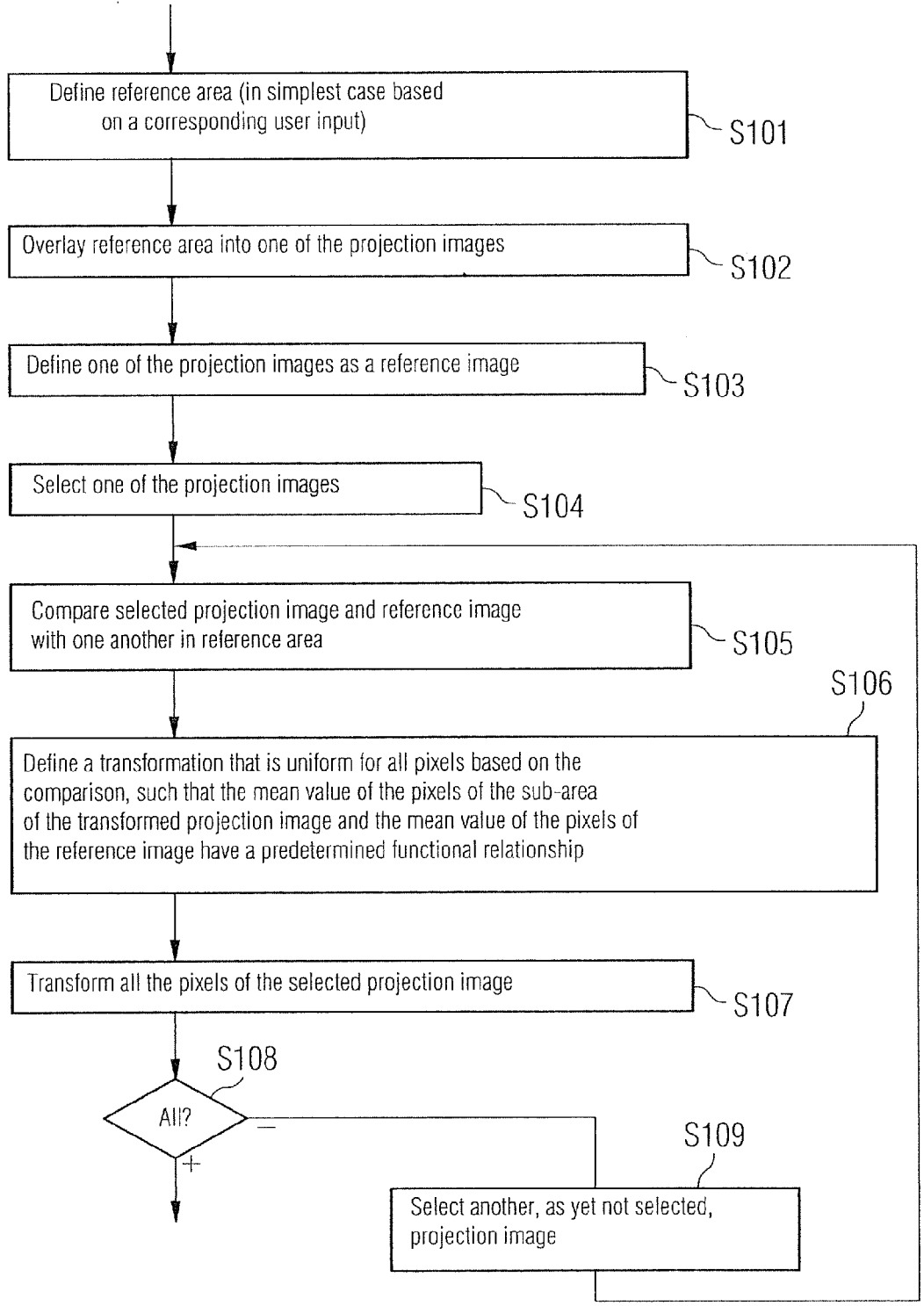

The essential difference between the present invention and the procedure in DE 10 2005 039 189.3 is the implementation of steps S35 to S37 in FIG. 6. These differences are examined in more detail below. The wording of DE 10 2005 039 189.3 and the reference characters used there (which were also used in FIGS. 1 to 18) are therefore retained, in as far as this is possible and expedient.

Figure 19:
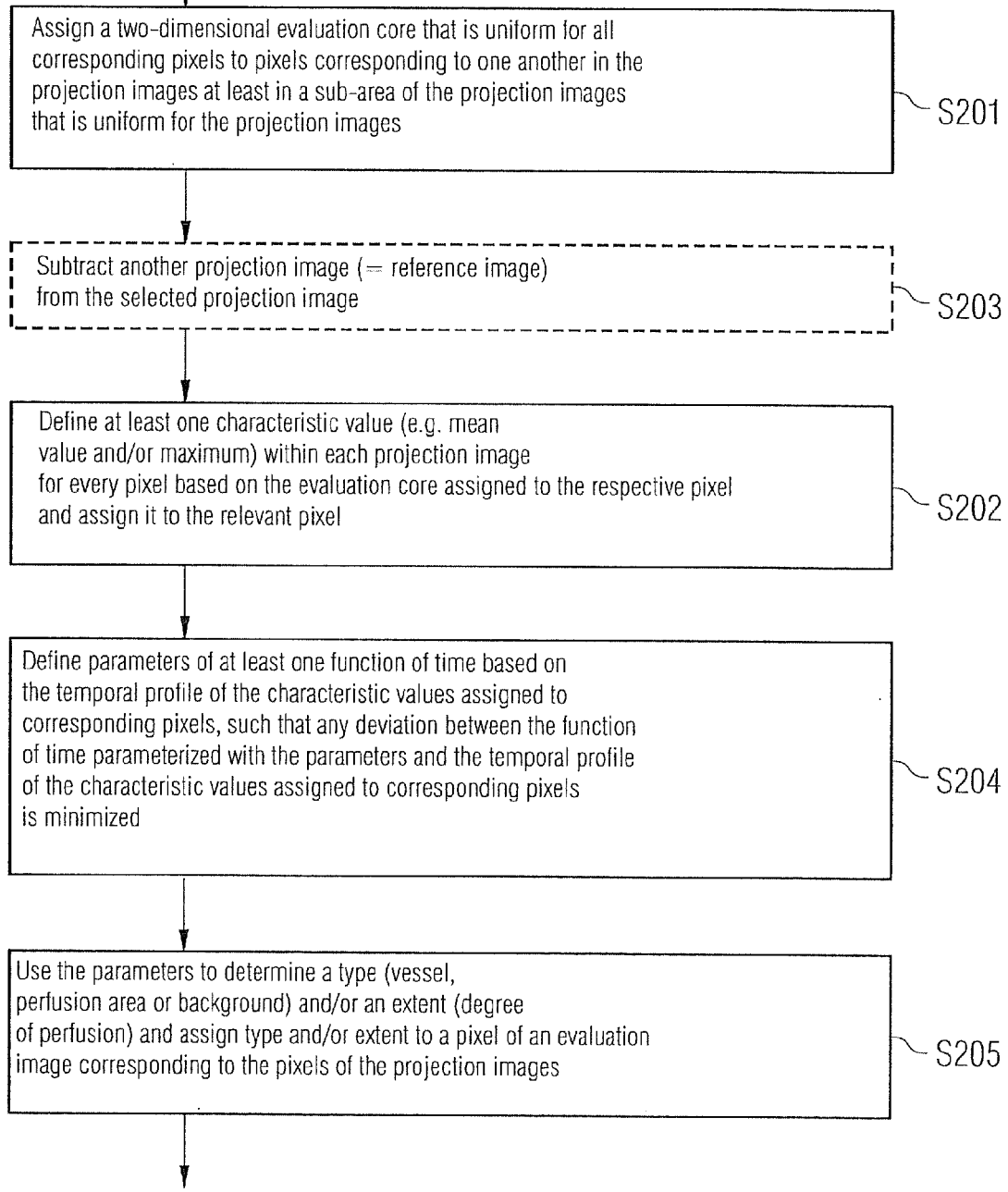

FIG. 19 shows a relatively general possibility for implementing steps S35 to S37 in FIG. 6 according to the present invention.

According to FIG. 19, in a step S201 the computer 8 defines an evaluation core 19 for each pixel 9 in the projection images B and assigns it to the relevant pixel 9. The evaluation core 19 is uniform for all pixels 9 corresponding to one another in the projection images B.

For example the computer 8 can define an individual evaluation core 19 for every pixel 9, comprising all the pixels 9, which are at a distance from the relevant pixel 9 within the projection images B, said distance not exceeding a maximum distance, or which are located in a parcel 19 of predefined contour, with the relevant pixel 9 being arranged in the center of this parcel 19.

In step S201 the computer 8 preferably subdivides the projection images B -as in the procedure in DE 10 2005 039 189.3—into two-dimensional parcels 19 and assigns the respective parcel 19 as an evaluation core 19 to each pixel 9 contained in a parcel 19. In this case the evaluation core 19 corresponds to the respective parcel 19.

In the case of parcel assignment the subsequent determination and assignment of type (vessel, perfusion area or background) and extent (or degree of perfusion) take place parcel by parcel. This significantly reduces computation outlay.

Figure 20:
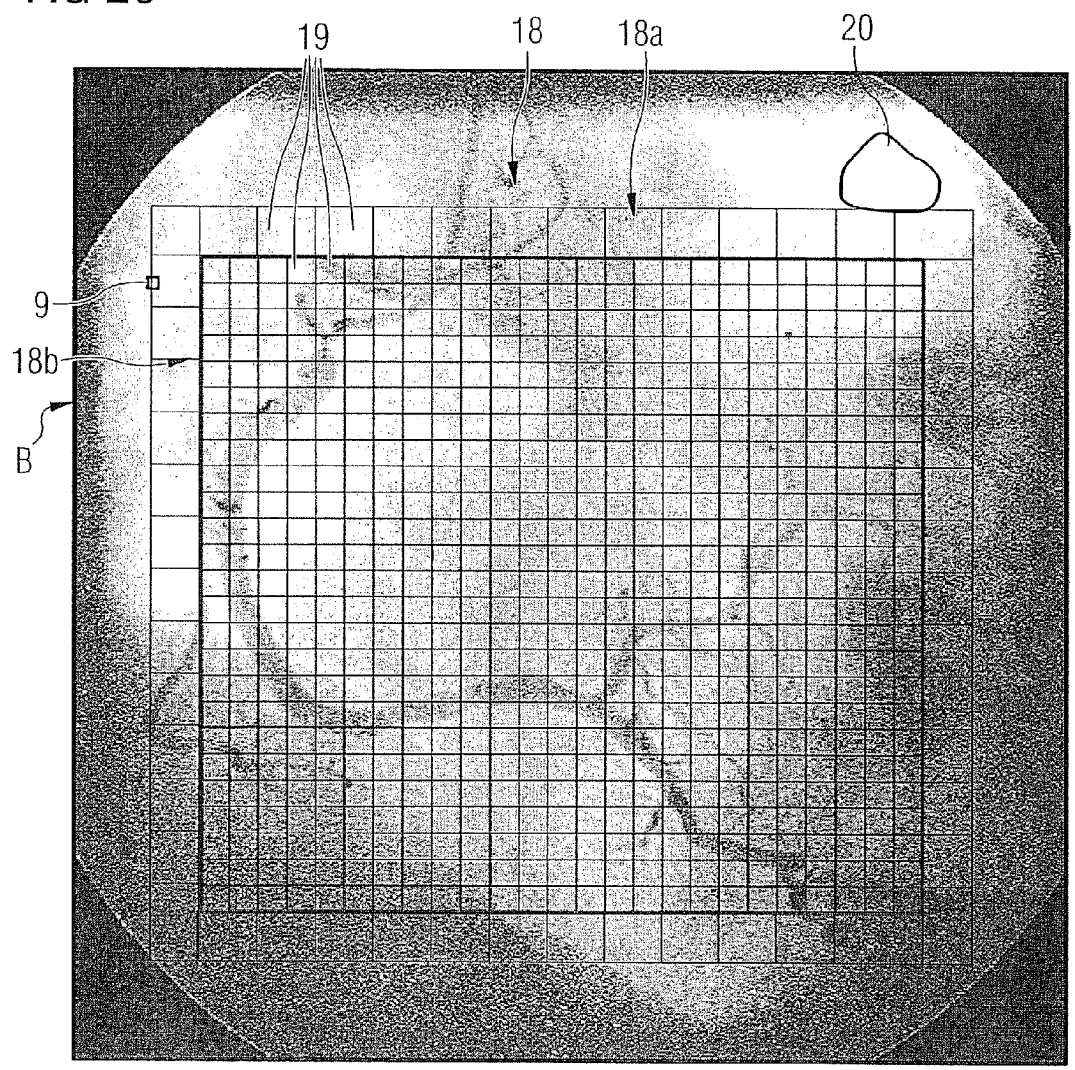
FIG. 20 shows a projection image.

The size of the evaluation core 19 can—with or without parceling—be independent of location. This case is shown by way of example in FIGS. 3, 7, 8 and 10. The size of the evaluation core 19 is preferably a function of its location. This is shown in FIG. 20.

In particular the size of the evaluation core 19 in an outer region 18a of the projection images B can be relatively large. For there is generally no relevant incorrect information contained there. A maximum size of for example 2,000 to 4,000 pixels should however not be exceeded even in the outer region.

In an inner region 18b of the projection images B the size of the evaluation core 19 should be smaller. For the relevant image information is generally contained in the inner region 18b. The size should however not be less than the minimum size of for example 16 to 65 pixels.

The inner region 18b can be predefined in a fixed manner for the computer 8. It is preferably defined automatically by the computer or predefined for the computer 8 by the user 6.

In step S201 the computer assigns the respective evaluation core 19 to the pixels 9 at least if the relevant pixels 9 are located in the sub-area 18 of the projection images B. The sub-area 18 can also be predefined in a fixed manner or can be defined by the user 6. It is also possible for the assignment of the evaluation cores 19 to take place in the projection images B as a whole. In any case the evaluation core 19 assigned to a specific pixel 9 is however uniform for all the projection images B.

In a step S202 the computer 8 defines at least one characteristic value C1, C2 within every projection image B for every pixel 9 (parcel by parcel in the case of the parcels 19) based on the evaluation core 19 (e.g. the respective parcel 19) assigned to the respective pixel 9 and assigns it to the respective pixel 9 (or the respective parcel 19). For example the computer 8 can—in the same manner as DE 10 2005 039 189.3—assign the mean value C1 of the pixel values of the pixels 9 contained in the relevant evaluation core 19 as the first characteristic value C1. Alternatively or additionally the computer 8 can assign the maximum of the pixel values of the pixels 9 contained in the relevant evaluation core 19 as the second characteristic value C2.

It is possible for the computer 8 to subtract another projection image B (hereafter referred to as reference image B) from the selected projection image B before determining the at least one characteristic value C1, C2. This is shown by a step S203 in FIG. 19. Step S203 is however only optional and therefore only shown in FIG. 19 with a dashed line.

In principle any projection image B can be a reference image B within the meaning of step S203. For example the first projection image B in time can be used. A specific reference image B can also be used for every projection image B.

In a step S204 the computer 8 defines parameters of at least one parameterizable function of time for every sequence of characteristic values C1, C2 (=for the temporal profile of the characteristic values C1, C2). Definition takes place in such a manner that any deviation between the functions of time parameterized with the parameters and the temporal profile of the corresponding characteristic value C1, C2 is minimized. Such a procedure is generally known as "fitting functions".

In the present case, in which the computer 8 determines both the first and second characteristic value C1, C2, the computer 8 uses the temporal profile of the first characteristic values C1 to determine parameters of at least one first function (hereafter referred to as the mean value function) and the temporal profile of the second characteristic values C2 to determine parameters of at least one second function (hereafter referred to as the maximum function).

Generally the number of parameters of the parameterizable functions is smaller than the number of projection images B. This is however not essentially so.

In a step S205 the computer 8 uses the parameters of the at least one mean value function and/or the parameters of the at least one maximum function to determine the type (vessel, perfusion area or background) and/or extent of perfusion of the respective pixel 9 and assigns the type and/or extent to the corresponding pixel 9 of the evaluation image A. If the assignment of type and/or extent takes place parcel by parcel, the determination of type and/or extent can of course also take place parcel by parcel.

After executing step S205 in FIG. 19, the computer outputs at least the sub-area 18 of the evaluation image A to the user 6 via a display device 16. This output takes place as in the procedure in DE 10 2005 039 189.3. The user 6 can optionally adjust the setting values as part of this output. For example the user 6 can predefine the limit time GZP and the threshold values SW1, SW2.

In DE 10 2005 039 189.3 the determination of type and degree of perfusion takes place solely based on the mean value (referred to there with the reference character M(j)) of the individual parcels 19. With the present invention the sequence of mean values M(j) corresponds to the sequence of first characteristic values C1.

Within the scope of the present invention it is also possible to work exclusively with the mean values C1. However a different procedure is preferred. This procedure is described below in conjunction with FIG. 21.

Figure 21:
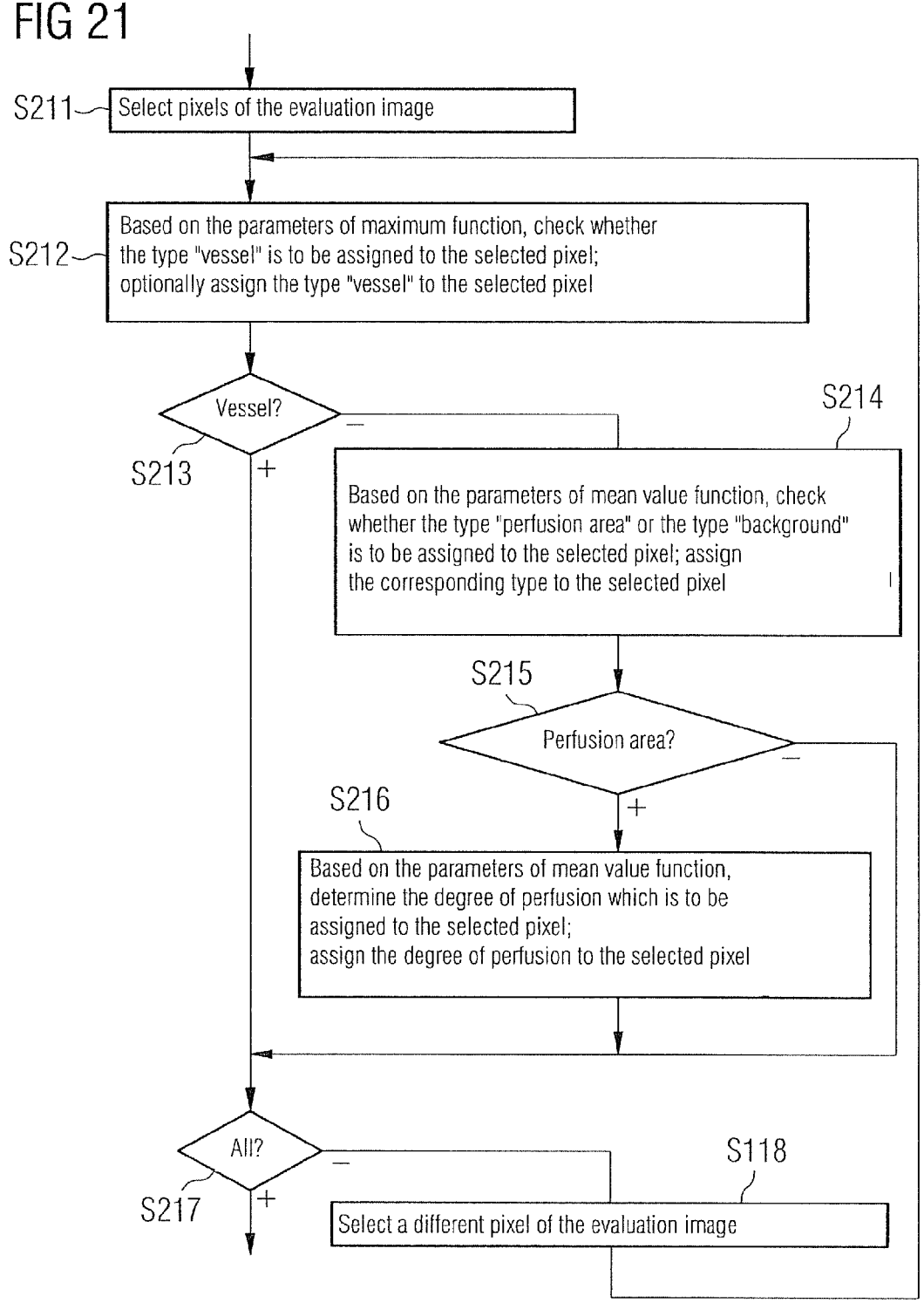
FIG. 21 shows a flow diagram.

FIG. 21 shows a possible refinement of step S205 in FIG. 19. According to FIG. 21 in a step S211 the computer 8 selects a pixel 9 of the evaluation image A. In a step S212 the computer 8 checks whether the type "vessel" is to be assigned to the selected pixel 9 and optionally assigns it to the selected pixel 9. Contrary to the doctrine of DE 10 2005 039 189.3 this check (optionally including assignment) takes place on the basis of the parameters of the maximum function.

In a step S213 the computer 8 checks whether it has assigned the type "vessel" to the selected pixel 9. If this is not the case, the computer moves on to a step S214. In step S214 the computer 8 determines whether it is to assign the type "perfusion area" or the type "background" to the selected pixel 9. Furthermore in step S214 it assigns the corresponding type to the selected pixel 9. The computer 8 preferably carries out this type definition and assignment based on the parameters of the mean value function.

In a step S215 the computer 8 checks whether it has assigned the type "perfusion area" to the selected pixel 9. If this is the case, the computer 8 moves on to a step S216. In step S216 the computer 8 determines which degree of perfusion it is to assign to the selected pixel 9. It also carries out the corresponding assignment in step S216. The determination in step S216 preferably also takes place based on the parameters of the mean value function.

If the computer 8 determines parameters of a number of mean value functions, the same or different mean value functions can alternatively be used for the type assignment (perfusion area or background) and extent assignment.

In a step S217 the computer 8 checks whether it has already carried out steps S212 to S216 for all the pixels 9 of the evaluation image A (or the sub-area 18 of the evaluation image A). If this is not the case, the computer 8 moves on to a step S218, in which it selects a different pixel 9 of the evaluation image A. From step S218 the computer 8 goes back to step S212. Otherwise the method according to FIG. 21 is terminated.

The procedure in FIG. 21 can be implemented parcel by parcel, if the projection images B and the evaluation image A are parceled.

Figure 22:
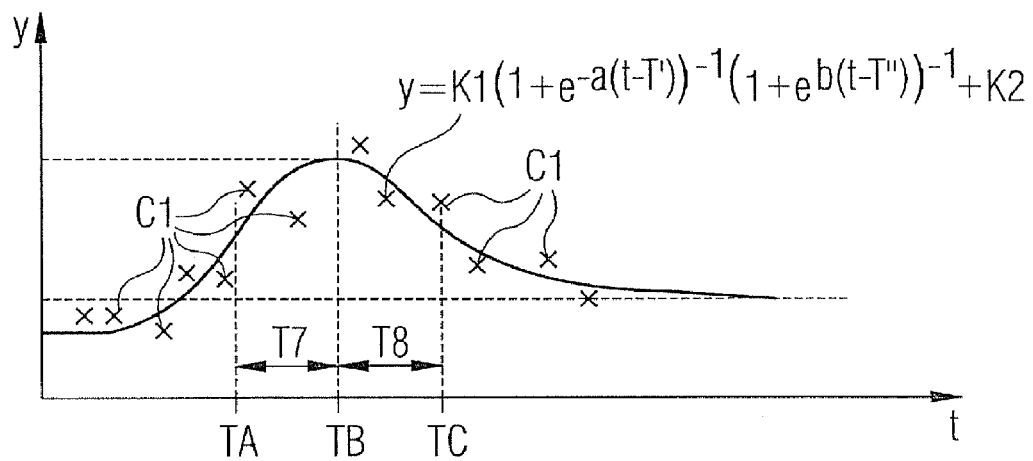
FIGS. 22 and 23 show time diagrams.

The mean value function, on the basis of which the computer 8 distinguishes the types "degree of perfusion" and "background" and on the basis of which primarily it determines and assigns the degree of perfusion, should preferably have the typical profile of what is known as a blush. The mean value function should therefore (independently of its specific parameterization) increase from an initial value to a maximum value and decrease from the maximum value to a final value, as time progresses. FIG. 22 shows such a function by way of example and also the mean values C1 of the corresponding evaluation cores 19 of the projection images B.

The exemplary mean value function in FIG. 22 has parameters K1, K2, a, b, T' and T". These parameters K1, K2, a, b, T', T" are optimized such that the deviation between the function of time parameterized with the parameters K1, K2, a, b, T', T" and the temporal profile of the mean values C1 is minimized.

As mentioned above, the computer 8 uses the parameters K1, K2, a, b, T', T" to determine a degree of perfusion and assigns the degree of perfusion to the respective parcel 19. For example the computer 8 can use the parameters K1, K2, a, b, T', T" to determine three times TA, TB, TC.

The time TB preferably corresponds to the time, when the mean value function reaches its maximum value.

The time TA can for example be defined in that the mean value function increases the most at time TA or that at time TA the mean value function has accomplished the increase from its initial value to its maximum value by a predefined percentage (in particular approx. 40 to 60%, e.g. 50%). The difference between the times TA, TB is characteristic of an input period T7, in which the contrast medium is input into the evaluation core 19 of the relevant pixel 9.

Similarly the time TC can for example be defined in that the mean value function decreases the most at time TC or that at time TC the mean value function has accomplished the decrease from its maximum value to its final value by a predefined percentage (in particular approx. 40 to 60%, e.g. 50%). The difference between the times TB and TC is characteristic of a washout time T8, in which the contrast medium is washed out of the evaluation core 19 of the relevant pixel 9.

The quotient (e.g. T8/T7) of and/or the difference (e.g. T8-T7) between the two periods T7, T8 in this case forms a good basis for determining the degree of perfusion. In particular TIMI blush grade 2 can be assigned to the respective parcel 19, if the quotient is within a predefined interval. If the quotient is outside the interval, TIMI blush grade 1 or TIMI blush grade 3 is assigned to the parcel 19. Whether TIMI blush grade 1 or TIMI blush grade 3 is assigned to the parcel 19 is a function of whether the quotient is greater than the upper limit of the interval or smaller than the lower limit of the interval. The interval limits can for example be defined on the basis of empirical values.

TIMI blush grade 0 cannot be determined with the last-described procedure. This can however be tolerated within the scope of the present invention, since within the scope of the present invention the type "background" is assigned to parcels 19, to which blush grade 0 should be assigned according to the TIMI classification.

The maximum function can have the same parameters as the mean value function. The specific values of the parameters in this case of course have to be defined independently of the parameters of the mean value function. To determine the parameters of the maximum function the first characteristic values C1 (in other words the means values) are in particular not used, but the second characteristic values C2 (in other words the maxima) are used.

Figure 23:
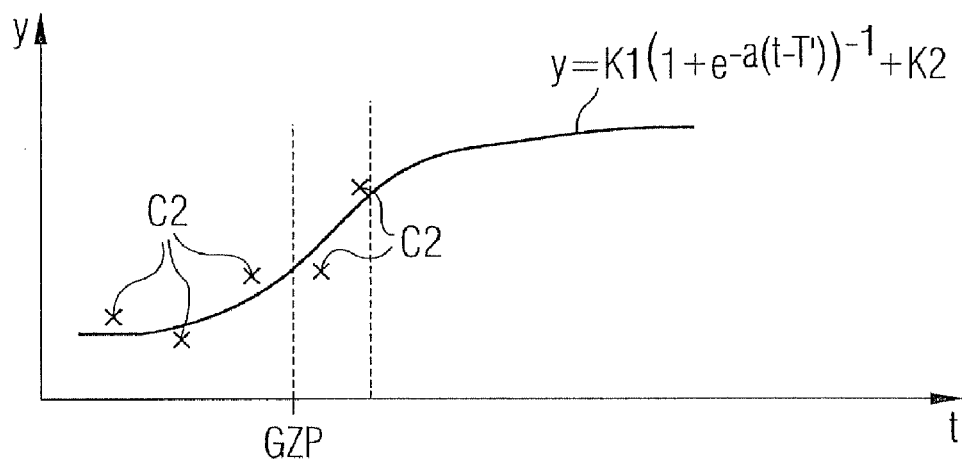

Alternatively it is possible for the computer 8 to determine the type "vessel" using a function which can be parameterized differently from the function used to distinguish between the types "background" and "perfusion area" and/or to determine the degree of perfusion. For example a function with the form $$y = K1 \cdot (1 + e^{-a(t-T')})^{-1} + K2$$

can be used to define the type "vessel". A function of this type is shown in FIG. 23.

It is furthermore possible, when distinguishing between the types "background" and "perfusion area" to use a function other than the function, on the basis of which the blush grade is defined. A specific parameterizable function can thus also be used for this function. In particular for example a function can be used, by means of which a linear (in particular constant profile) can be clearly identified with statistical scattering around the straight line thus defined. It is possible in this manner for example to determine parcels 19 of the type "background". Once the parcels of the type "vessel" and the parcels 19 of the type "background" have been determined, in this case the remaining parcels 19 must be of the type "perfusion area".

As a rule—as already described from the start in DE 10 2005 039 189.3—the computer 8 only assigns the type "vessel" to a pixel 9 (or a parcel 19) of the evaluation image A, if the temporal profile of the characteristic values C1, C2 shows a predefined minimum increase before the limit time GZP, for example (see also FIG. 12) exceeding the threshold value SW1. It is therefore possible for the computer in accordance with FIG. 24 in a step S221 to select the characteristic values C1, C2 of the projection images B, which are before the limit time GZP in time or are as a maximum a time limit behind the limit time GZP in time.

The time limit is preferably defined such that only one or maximum two projection images B are taken into account, which are behind the limit time GZP in time. The reason for taking these projection images B into account is that it is easier to identify from these projection images B behind the limit time GZP, whether there is actually a significant increase before the limit time GZP or whether it is simply an outlier (see also FIG. 16). In some instances outliers can be identified in this manner and not be taken into account.

In a step S222 the computer 8 determines parameters of at least one function of time based on the temporal profile of the selected characteristic values C1, C2. In particular the computer 8 can for example define parameters K1, K2, a, T' of a corresponding maximum function based on the second characteristic values C2.

Figure 24:
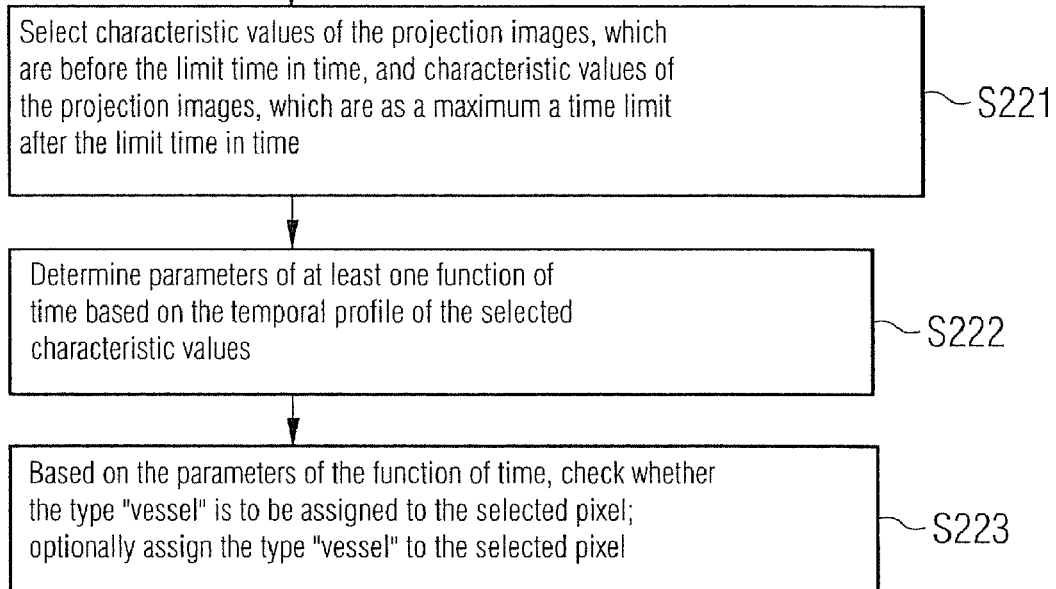

The procedure according to FIG. 24 can be realized with the first characteristic values C1, which are characteristic of the mean values of the evaluation cores 19. However it is preferably realized with the second characteristic values C2, which are characteristic of the maxima of the evaluation cores 19.

In a step S223 the computer 8 checks—e.g. based on the parameters K1, K2, a, T' defined in step S222—whether the type "vessel" is to be assigned to the respective pixel 9 and optionally carries out this assignment.

It is in particular possible to identify arteries using the procedure described above. In order also to be able to identify veins, it is possible also to assign the type "vessel" to a parcel 19, if the above-mentioned minimum increase (or a slightly smaller increase) only occurs after a further limit time, which is a sufficiently long time after the first-mentioned limit time GZP.

To determine the mean values (in other words the first characteristic values C1) of the individual evaluation cores 19, it is usually possible to form the general mean value (in other words taking into account all pixel values). The mean value C1 is preferably determined in such a manner, as described below in conjunction with FIGS. 25 and 26.

Figure 25:
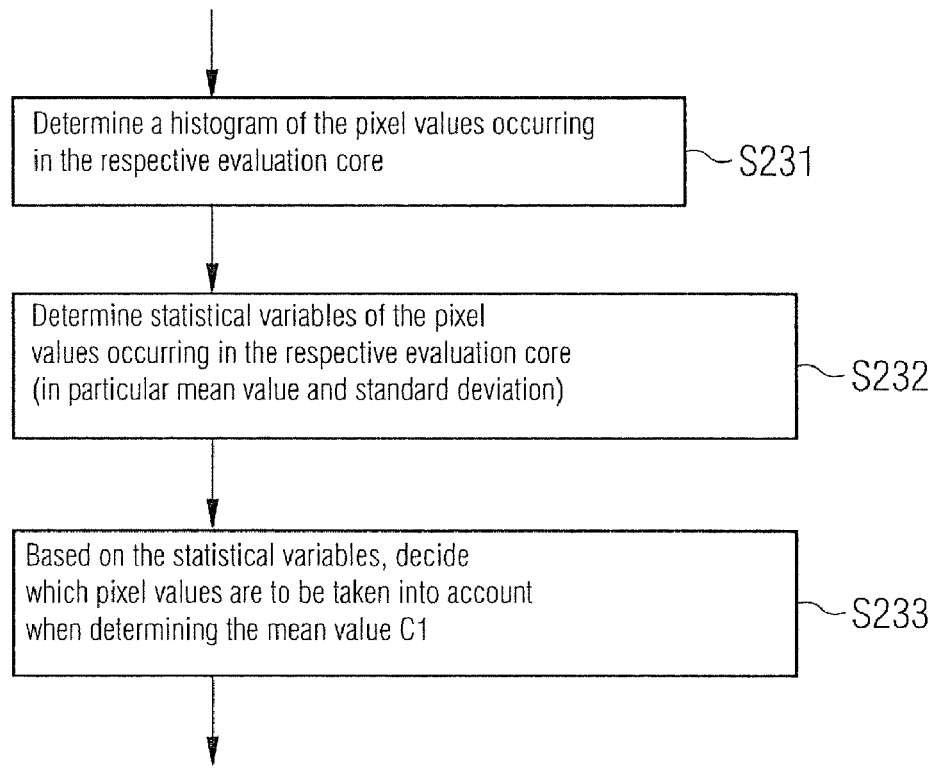
Figure 26:
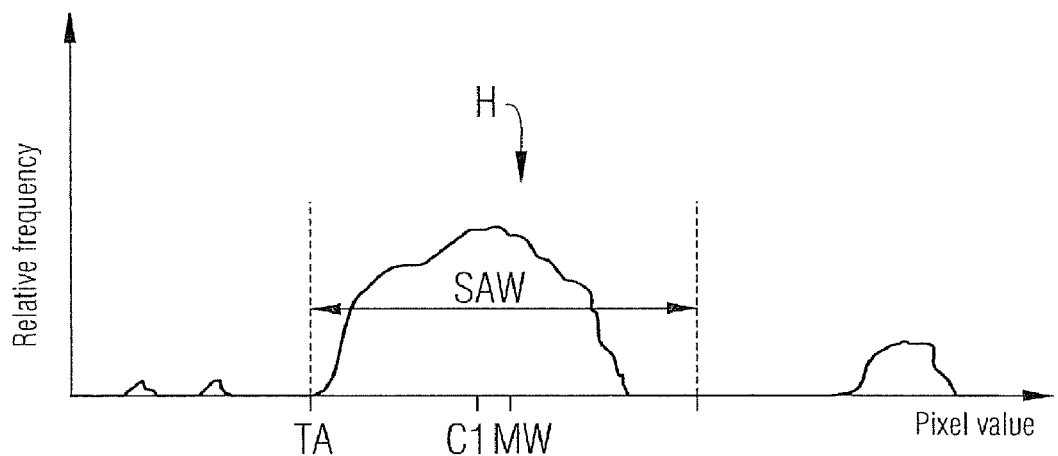
FIG. 26 shows an evaluation core and a histogram.

According to FIG. 25 in a step S231 the computer 8 determines a histogram H of the pixel values occurring in the respective evaluation core 19. An example of such a histogram H is shown in FIG. 26.

In a step S232 the computer 8 determines statistical variables of the histogram H. In particular the computer 8 can determine the mean value MW and the standard deviation SAW of the pixel values of the respective evaluation core 19. All the pixel values occurring are taken into account when determining the mean value MW.

In a step S233 the computer 8 decides, based on the statistical variables MW, SAW, which of the pixel values it takes into account when determining the first characteristic value C1. For example it may only take into account pixel values, which deviate from the mean value MW by less than the standard deviation SAW.

The procedure described above already provides a very good outcome. The procedure can however be even further optimized.

Thus it is for example possible for the computer 8 to determine the size of the evaluation core 19 iteratively based on the type assigned to the pixels 9, at least for some of the pixels 9. This procedure can be expedient in particular for the pixels 9, to which the type "vessel" is assigned. This is described in more detail below in conjunction with FIGS. 27 and 28 for a parcel 19. The procedure in FIGS. 27 and 28 could also be realized, if the evaluation core 19 was defined individually for each individual pixel 9.

Figure 28:
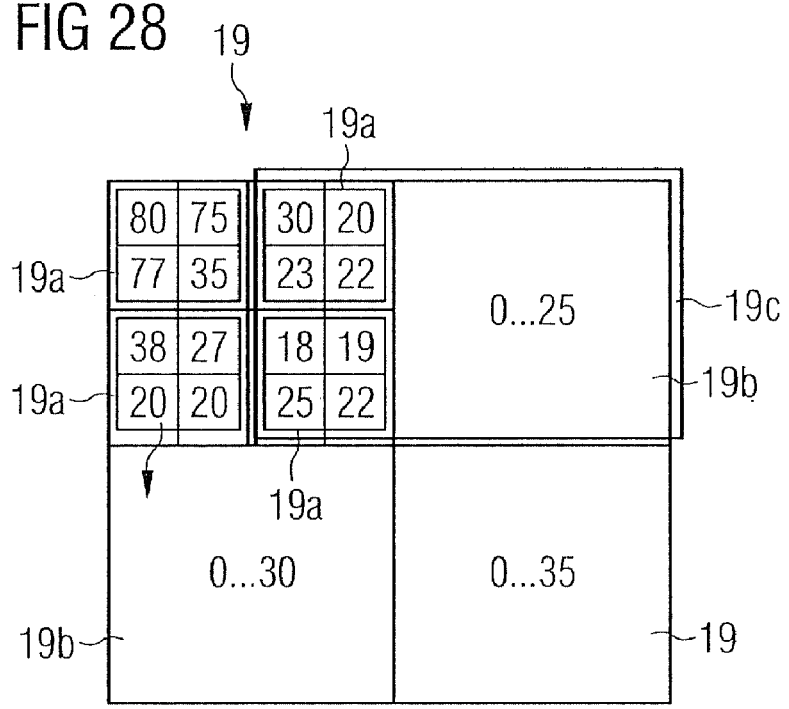
FIG. 28 shows parcels

FIG. 27 shows a possible detailed refinement of steps S201 to S205 in FIG. 19. The difference formation, which is in principle possible in step S203 in FIG. 19 is not shown in FIG. 27. FIG. 28 shows a number of parcels 19.

According to FIG. 27 in a step S241 the computer 8 subdivides the projection images B into parcels 19. In a step S242 the computer 8 determines for every parcel 19, whether the type "vessel" is to be assigned to the respective parcel 19. For example it determines the maximum function, as in steps S211 and S212 in FIG. 21, and checks whether the maximum function increases to above the first threshold value SW1 before the limit time GZP in accordance with steps S2221 to S223 in FIG. 24. The computer 8 optionally assigns the type "vessel" temporarily to the parcels 19 as part of step S242.

In a step S243 the computer 8 selects a parcel 19, to which the type "vessel" is temporarily assigned. In a step S244 the computer 8 checks whether the selected parcel 19 exceeds a minimum size. The minimum size can be between 60 and 250 pixels for example.

If the size of the parcel 19 does not exceed the minimum size, the computer 8 finally assigns the type "vessel" to the selected parcel 19 in a step S245.

If the size of the selected parcel 19 exceeds the minimum size, in a step S246 the computer 8 defines an angle range, in which the selected parcel 19 is surrounded by parcels 19, to which the type "vessel" is not assigned, neither temporally nor finally. The center (=vertex), in relation to which the angle range is determined, is located within the selected parcel 19, in particular in the center of mass.

In a step S247 the computer 9 checks whether the angle range defined in step S246 is greater than a first minimum angle range. If this is not the case, the computer 8 assigns the type "vessel" finally to the relevant parcel 19 in a step S248.

The first minimum angle range can for example be 90° or 180°. It can also have any intermediate value. It can also be sufficient, if the selected parcel 19 is adjacent to at least one further parcel 19, to which the type "vessel" is assigned neither temporarily nor finally.

If the first minimum angle range is exceeded, in a step S249 the computer 8 subdivides the selected parcel 19 into sub-parcels 19a. In a step S250 the computer 8 also assigns the type "vessel" temporarily to the sub-parcels 19. The sub-parcels 19a are processed in the same manner as normal parcels 19 for the further method in FIG. 27.

In a step S251 the computer 8 checks whether all the parcels 19, to which the type "vessel" is assigned, have already been finally assigned this type. If this is not the case, the computer 8 goes back to step S243.

FIG. 28 shows by way of example the advantage of the procedure in FIG. 27. In accordance with FIG. 28, the selected parcel 19 is divided—purely by way of example—into four equally sized sub-parcels 19a. If it is assumed for example that a parcel 19 is identified as a vessel, if the maximum of the pixel values exceeds the value 40, in the example in FIG. 28 only the left upper sub-parcel 19a would have to be classified as a vessel. The three other sub-parcels 19a would either be background or perfusion area.

The procedure shown in FIG. 28 is not the only one possible. It would for example also be possible, in the case of the parcel 19 in FIG. 28, gradually to reduce the parcel 19 slightly at each edge or each corner and to check whether the part of the parcel 19, which is now no longer contained in the reduced parcel 19a, should not be classified as a vessel. It would be possible in this manner to draw a more precise boundary, which could possibly be accurate to one pixel.

As part of the procedure in FIG. 27, as described above in conjunction with FIG. 28, the computer 8 as a rule does not also finally assign the type "vessel" in full to all the parcels 19, to which the type "vessel" is temporally assigned. As a rule sub-parcels 19a result, to which the type "vessel" is not assigned. It is possible to process the resulting sub-parcels 19a as independent parcels 19, to which the computer 8 later assigns one of the types "perfusion area" or "background". It is also possible to combine the sub-parcels 19a with an adjacent parcel 19, to which the type "vessel" is not assigned (neither temporarily nor finally) to form an overall parcel 19c. This is described in more detail below in conjunction with FIGS. 28 and 29.

FIG. 29 shows a modification of steps S249 to S251 in FIG. 27. In accordance with FIG. 29 step S250 can be replaced by steps S261 to S264.

In step S261 the computer 8 determines those of the sub-parcels 19a, to which the type "vessel" is to be assigned and assigns the type "vessel" temporarily to said sub-parcels 19a.

The remaining sub-parcels 19a, to which the type "vessel" is not temporarily assigned, are combined by the computer 8 in step S262 with an adjacent parcel 19b, to which the type "vessel" is also not assigned (neither temporarily nor finally) to form an overall parcel 19c.

It is possible always to execute the step S262. It is also possible to check, before executing step S262, whether the resulting overall parcel 19c exceeds a maximum size, and then only to carry out the combination, if the maximum size is not exceeded. The check to determine whether the maximum size is exceeded preferably takes place after the combination of the parcels 19a, 19b. In this case the computer 8 checks in step S263, whether the overall parcel 19c exceeds the maximum size. If this is the case, the computer 8 divides the overall parcel 19c in step S264 into two parcels 19, preferably having an identical size.

As already described in conjunction with FIG. 21, the computer 8 assigns either the type "perfusion area" or the type "background" to the parcels 19, to which it does not assign the type "vessel". It also assigns a degree of perfusion to the parcels 19 of the type perfusion area. This procedure, described in principle in conjunction with FIG. 21, can also be further optimized. This is described in more detail below in conjunction with FIG. 30. It is pointed out earlier in this context that as part of the procedure in FIG. 30 the assignment of the type "perfusion area" is initially only temporary. It is also assumed in the context of FIG. 30 that the parcels 19 have already been assigned their type.

FIG. 30 shows a possible implementation of steps 214 to S217 in FIG-21. In accordance with FIG. 30 in a step S271 the computer 8 selects a parcel 19 of the type "perfusion area". In a step S272 the computer 8 determines a logical variable OK for the selected parcel 19. The logical variable OK assumes the value "TRUE" if, and only if, an angle range, in which the selected parcel 19 is completely surrounded by parcels 19 of the type "background", is greater than a second minimum angle range. The angle range is determined as in step S246 in FIG. 27.

The second minimum angle range is as a rule greater than the first minimum angle range. In extreme cases it can be so great that the logical variable OK can only assume the value "TRUE", if the selected parcel 19 is completely surrounded by parcels 19 of the type "background".

In a step S273 the computer 8 checks the value of the logical variable OK. If the logical variable OK has the value "TRUE", the computer 8 moves on to a step S274. In step S274 the computer 8 checks whether the selected parcel 19 is completely surrounded by parcels 19 of the type "background". If this is the case, the computer 8 moves on to a step S275, in which it assigns the type "background" to the selected parcel 19.

If the selected parcel 19 is not completely surrounded by parcels 19 of the type "background", the computer 8 moves on to a step S276. In step S276 the computer 8 checks whether the characteristic values C1, C2 of the selected parcel 19 of the projection images B (or variables derived therefrom, for example the parameters of the mean value function and/or the maximum function) satisfy a change condition. If the change condition is satisfied, the computer 8 also moves on to step S275.

If the change condition is not satisfied, or if the logical variable OK has the value "UNTRUE", the computer 8 moves on to a step S277. In step S277 the computer 8 determines the degree of perfusion and assigns it to the corresponding parcel 19. It also assigns the type "perfusion area" finally to the selected parcel 19.

In a step S278 the computer 8 checks whether it has already carried out steps S271 to S277 for all the parcels 19 of the type "perfusion area". If this is not the case, the computer 8 goes back to step S271. Otherwise the procedure is terminated in accordance with FIG. 30.

Step S274 in FIG. 30 is only optional. It can therefore be omitted. In particular step S274 is meaningless, if the check in step S274 is already implied in step S273.

If step S274 is omitted, step S276 can be inserted between steps S273 and S275. It can alternatively be omitted.

Figure 31:
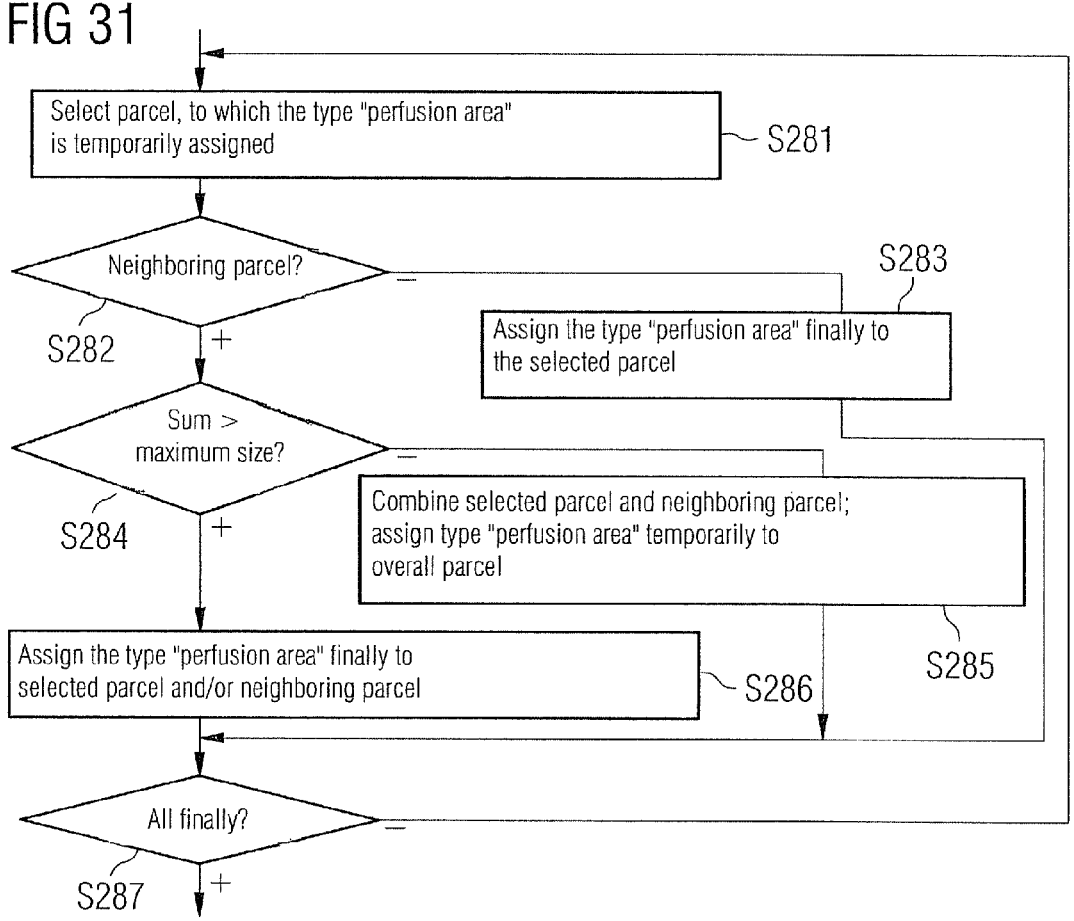
FIG. 31 shows a flow diagram for determining an optimization.

Determination of the degree of perfusion can be optimized. This is described in more detail below in conjunction with FIG. 31. In the context of FIG. 31 it is assumed that the assignment of the type "perfusion area" to the parcels 19 is at first only temporary.

The method in accordance with FIG. 31 can be realized independently of the method in FIG. 30. If it is combined with the method in FIG. 30, it follows the method in accordance with FIG. 30. In this case step S277 in FIG. 30 is omitted, in so far as it relates to the determination and assignment of the degree of perfusion. For this reason step S277 in FIG. 30 is only shown with a broken line.

In accordance with FIG. 31 in a step S281 the computer 8 selects a parcel 19, to which the type "perfusion area" is temporarily assigned.

In a step S282 the computer 8 checks whether a neighboring parcel 19, to which the type "perfusion area" is similarly (temporarily or finally) assigned, exists next to the selected parcel 19. If this check is negative, in a step S283 the computer assigns the type "perfusion area" finally to the selected parcel 19.

If the computer 8 finds a neighboring parcel 19, in a step S284 the computer 8 checks whether the sum of the sizes of the selected parcel 19 and the neighboring parcel 19 exceeds a maximum size. If this is the case, in a step S285 the computer 8 assigns the type "perfusion area" finally to at least one of the two parcels 19. Otherwise the computer 8 combines the selected parcel 19 and the neighboring parcel 19 in a step S286 to form an overall parcel 19c and assigns the type "perfusion area" temporarily to this.

In a step S287 the computer 8 checks whether it has already finally assigned the type "perfusion area" to all the parcels 19, to which the type "perfusion area" was initially temporarily assigned.

The maximum size in step S284 can be constant. Alternatively it is however possible for the computer 8, before executing the method in FIG. 31, to determine internally related areas of the evaluation image A, in which it has assigned exclusively the type "perfusion area" to the parcels 19. In this case the computer 8 can for example define the maximum size of the parcels 19 of the respective area as a function of the size of the respective area. In particular it can select the maximum size to be even smaller, the smaller the respective internally related area.

It is also possible for the computer 8, after assigning the type "vessel" to the parcels 19 (optionally including subsequent optimization of said parcels 19, see also FIG. 28) to re-divide the remaining parcels 19. In this case the computer

8 can select the parcel size of the remaining parcels 19 to be even smaller, the smaller the distance between the remaining parcels 19 and the parcels 19, to which the type "vessel" is assigned.

The procedures described to date are based totally on the definition of evaluation cores 19 and the use of characteristic variables C1, C2, which were determined based on the evaluation cores 19. The assignment of the type "vessel" to the parcels 19 can in particular be even further optimized in a different manner. This is described in more detail below in conjunction with FIG. 32.

Figure 32:
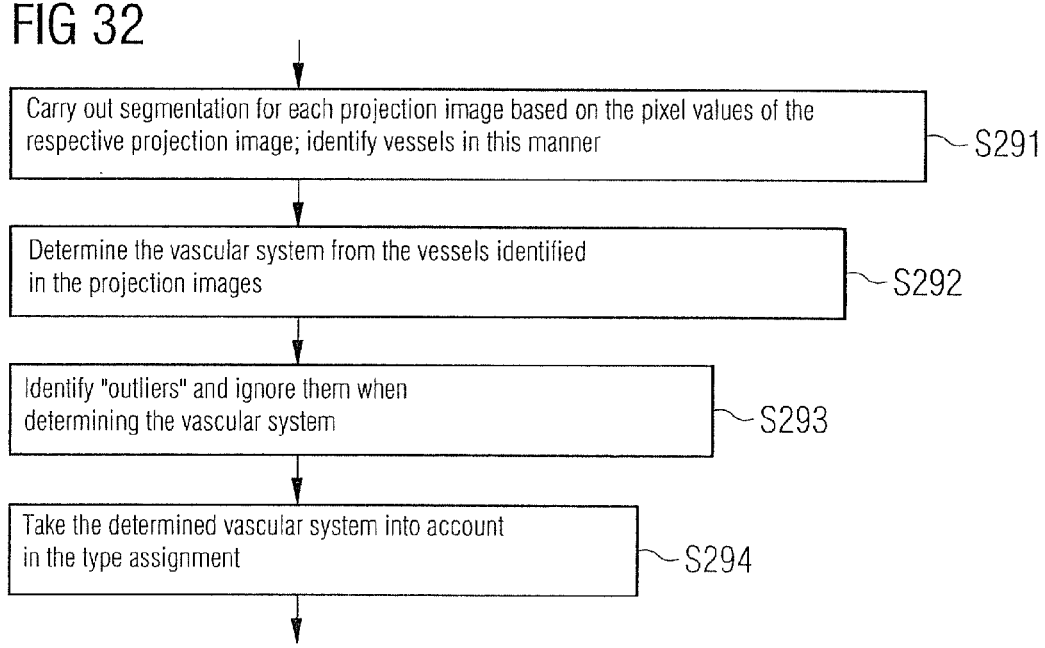
FIG. 32 shows a further flow diagram for determining an optimization

In accordance with FIG. 32 in a step S291 the computer 8 carries out a vessel segmentation for each projection image B based on the pixel values of the respective projection image B—in other words without parceling or assignment of evaluation cores 19 and without evaluation of temporal profiles. In this manner it identifies vessels of the vascular system. Vessel segmentations are generally known. There is therefore no need to examine such procedures in more detail here.

In a step S292 the computer 8 determines the vascular system from the vessels identified in the projection images B. For example the vascular system can be determined by adding together the vessels identified in the individual projection images B.

If necessary, in a step S293 the computer 8 clears the vascular system determined in step S292 of "outliers". For example image areas identified originally as vessel can be deleted, if identification as a vessel only took place in a single or only in two projection images B.

In a step S294 the computer 8 takes into account the vascular system determined in step S292 (optionally including step S293) in the type assignment for the parcels 19. For example the computer 8 can assign the type "vessel" beforehand to specific pixels 9 (even finally) and/or can shape the parcels 19 correspondingly.

The inventive image evaluation method demonstrates a high degree of automation and a high processing speed. It is also very flexible, even in the context of visualizing the evaluation result and in the context of interactivity. Finally it is also possible to integrate the inventive image evaluation method as part of what is known as TIMI flow measurement. This avoids duplicated capturing of the projection images B and the x-ray load for the patient 3 associated therewith.

The above description serves exclusively to explain the present invention. The scope of protection of the present invention should however only be defined by the accompanying claims.

The invention claimed is:

1. An image evaluation method for two-dimensional projection images to show a temporal profile of a distribution of a contrast medium in an examination object, wherein the examination object has a vascular system and a surrounding, wherein each projection image comprises a plurality of pixels with pixel values, wherein the pixel values of pixels corresponding to one another in the projection images are defined by at least essentially locationally identical areas of the examination object, comprising:
    assigning a uniform two-dimensional image evaluation core for all corresponding pixels to pixels corresponding to one another in the projection images at least in a sub-area of the projection images that is uniform for the projection images;
    determining at least one characteristic value for the pixel within the projection image based upon the evaluation core assigned to the pixel within the projection image;
    assigning the characteristic value to the pixel within the projection image;
    determining parameters of a function in time based upon a temporal profile of characteristic values assigned to corresponding pixels to minimize a deviation between the function of time parameterized with the parameters and the temporal profile of the characteristic values assigned to corresponding pixels;
    defining a type or an extent based upon the parameters and assigning the type or extent to a pixel of a two-dimensional evaluation image, wherein the type is distinctive of whether the respective pixel of the evaluation image corresponds to a vessel of the vascular system, a perfused part of the surroundings of a vessel of the vascular system or a non-perfused part of the surroundings of a vessel of the vascular system, and wherein the extent is distinctive for an extent of perfusion; and
    outputting at least the sub-area of the evaluation image to a user via a display device.

2. The image evaluation method as claimed in claim 1, wherein a computer assigns a maximum of the pixel values in the evaluation core assigned to the respective pixel to the pixels as a characteristic value.

3. The image evaluation method as claimed in claim 2, wherein the computer defines parameters of a maximum function based upon a temporal profile of the maximums to minimize a deviation between the function of time parameterized with the parameters and the temporal profile of the maximum, and wherein the computer determines based upon the parameters whether the type "vessel" is assigned to the corresponding pixel of the evaluation image.

4. The image evaluation method as claimed in claim 1, wherein a mean value of the pixel values occurring in the evaluation core assigned to the respective pixel is assigned to the pixels as a distinctive value.

5. The image evaluation method as claimed in claim 4, wherein parameters of a mean value function are determined based upon the temporal profile of the mean value to minimize a deviation between the mean value function parameterized with the parameters and the temporal profile of the mean value, and wherein an assignment of a perfusion area type or a background type to the corresponding pixel of the evaluation image is determined based upon the parameters of the mean value function.

6. The image evaluation method as claimed in claim 4, wherein parameters of a mean value function are determined based upon the temporal profile of the mean value to minimize a deviation between the mean value function parameterized with the parameters and the temporal profile of the mean value, and wherein a degree of perfusion is assigned to the corresponding pixel of the evaluation image based upon the parameters of the mean value function.

7. The image evaluation method as claimed in claim 6, wherein a computer determines an input period characteristic of the input of the contrast medium into the corresponding evaluation core based upon the parameters, wherein a washout period characteristic of a washing out of the contrast medium from the corresponding evaluation core for a pixel under consideration is determined, and wherein a degree of perfusion is determined based upon the input and the washout period.

8. The image evaluation method as claimed in claim 6, wherein a computer only assigns the type vessel to the pixels of the evaluation image, if the parameterized function of time has a predefined minimum increase before a limit time, wherein the computer defines the parameters of the function exclusively based on the characteristic values of the pixels of the projection images, which are before the limit time in time, and the projection images, which are as a maximum a predefined time limit after the limit time in time, and wherein the computer assigns the type vessel based upon the defined parameters.

9. The image evaluation method as claimed in claim 6, wherein the number of parameters of the parameterizable function is smaller than the number of projection images.

10. The image evaluation method as claimed in claim 4, wherein a histogram of the pixel values in the evaluation core is determined do determine the mean value based upon the histogram.

11. The image evaluation method as claimed in claim 10, wherein statistical variables related to the distribution of the pixel values are determined based upon the histogram and wherein a consideration of pixel values for determining the mean value is based upon the statistical variables.

12. The image evaluation method as claimed in claim 1, wherein the parameterizable function increases from an initial value to a maximum value and decreases from the maximum value to a final value, as time progresses.

13. The image evaluation method as claimed in claim 12, wherein the function has the form $$y = K1 \cdot (1+e^{-a(t-T')})^{-1} \cdot (1+e^{b(t-T'')})^{-1} + K2,$$

where y is a function value, t a time and $K1$, $K2$, $a$, $b$, $T'$, $T''$ the parameters of the function.

14. The image evaluation method as claimed in claim 1, wherein a size of the evaluation core is a function of a location of the evaluation core.

15. The image evaluation method as claimed in claim 1, wherein a computer determines the size of the evaluation core iteratively based upon the type assigned to the pixels.

16. The image evaluation method as claimed in claim 15, wherein the computer assigns a type to a parcel, wherein in a iteration the type vessel is assigned, wherein the parcel with the type vessel is subdivided in sub parcels if the parcel is greater than a minimum size and the computer makes a further iteration if the parcel is surrounded by further parcels in an angle range greater than a first minimum angle range, wherein the type vessel is not assigned to the further parcels in a foregoing iteration.

17. The image evaluation method as claimed in claim 16, wherein sub-parcels not assign to the type vessel in the further iteration are combined, wherein the sub-parcel is combined with a parcel not assigned to the type vessel and adjacent to the sub-parcel to form an overall parcel.

18. The image evaluation method as claimed in claim 1, wherein a computer subdivides the projection images and the evaluation image into parcels, wherein the computer determines the type assignment or the extent assignment parcel by parcel, and wherein the evaluation core corresponds to the respective parcel.

19. The image evaluation method as claimed in claim 18, wherein a computer combines mutually adjacent parcels of the same type to form an overall parcel.

20. The image evaluation method as claimed in one of claim 18, wherein the assignment type of parcels assigned to a perfusion area type is changed to a background assignment type, if the parcel is surrounded in an angle range, which is greater than a second minimum angle range, by parcels assigned to the type background.

21. The image evaluation method as claimed in claim 20, wherein the change of type is made, if the parcel is surrounded exclusively by parcels of the type background or if characteristic values of the parcel under consideration satisfy a change condition.

22. The image evaluation method as claimed in claim 18, wherein a computer determines internally related areas of the evaluation image, in which it has assigned exclusively the type perfusion area to the parcels, and wherein the computer defines the size of the parcel within the respective area as a function of the size of the respective area.

23. The image evaluation method as claimed in claim 1, wherein a computer makes a vessel segmentation for each projection image based upon pixel values of the projection image and assigns a type based upon identified vessels, wherein the vessels are identified based on the vessel segmentation.

24. The image evaluation method as claimed in claim 23, wherein the computer determines the vascular system from the vessels identified in the projection images and takes the determined vascular system into account in the type assignment.

25. The image evaluation method as claimed in claim 1, wherein at least two different parameterizable functions are used to define the individual types or the degree of perfusion.

* * * * *